(12) United States Patent
Ancar

(10) Patent No.: US 9,788,810 B2
(45) Date of Patent: Oct. 17, 2017

(54) SYSTEM AND METHOD FOR X-RAY IMAGING ALIGNMENT

(71) Applicant: Terry L Ancar, Kenner, LA (US)

(72) Inventor: Terry L Ancar, Kenner, LA (US)

(73) Assignee: PORTAVISION MEDICAL LLC, Kenner, LA (US)

( * ) Notice: Subject to any disclaimer, the term of this patent is extended or adjusted under 35 U.S.C. 154(b) by 0 days.

(21) Appl. No.: 15/191,449

(22) Filed: Jun. 23, 2016

(65) Prior Publication Data

US 2016/0374641 A1    Dec. 29, 2016

Related U.S. Application Data

(60) Provisional application No. 62/184,554, filed on Jun. 25, 2015.

(51) Int. Cl.
A61B 6/10    (2006.01)
A61B 6/00    (2006.01)

(52) U.S. Cl.
CPC ............ A61B 6/587 (2013.01); A61B 6/4405 (2013.01); A61B 6/4452 (2013.01); A61B 6/488 (2013.01)

(58) Field of Classification Search
CPC ...... G01N 23/04; G01N 23/043; G01N 23/08; G01N 23/083; A61B 6/06; A61B 6/08; A61B 6/10; A61B 6/107; A61B 6/4405; A61B 6/4411; A61B 6/4452; A61B 6/587; H05G 1/54; H05G 1/56; G21K 1/02; G21K 1/025; G21K 1/04; A61N 5/1049
USPC ......... 378/62, 117, 147, 148, 150, 205, 206, 378/207
See application file for complete search history.

(56) References Cited

U.S. PATENT DOCUMENTS

| | | | | |
|---|---|---|---|---|
| 5,315,630 A * | 5/1994 | Sturm | ...................... | A61B 6/08 378/205 |
| 7,488,107 B2 * | 2/2009 | Tubbs | ...................... | A61B 6/08 378/205 |
| 7,581,885 B2 * | 9/2009 | Ertel | ........................ | A61B 6/08 378/204 |
| 8,873,712 B2 * | 10/2014 | Wang | ...................... | A61B 6/08 378/108 |

* cited by examiner

Primary Examiner — Jurie Yun
(74) Attorney, Agent, or Firm — Marin Patents LP; Gustavo Marin

(57) ABSTRACT

The present invention provides a positioning system comprising at least a portable detector that enables users to continuously know the spatial location of a detector relative to an x-ray source so that it can be more easily aligned, and monitored for maintenance of alignment, with the portable detector within predetermined tolerances during procedures. In preferred embodiments, the invention further comprises a radiation interlock switch to prevent the emission of radiation in the event of the x-ray source and detector not being aligned within a predetermine tolerance.

15 Claims, 33 Drawing Sheets

SYSTEM AND METHOD FOR X-RAY IMAGING ALIGNMENT

CROSS-REFERENCE TO RELATED APPLICATIONS

This application claims priority to U.S. provisional application 62/184,554 filed on Jun. 25, 2015, the entire specification of which is incorporated herein by reference.

REFERENCE TO GOVERNMENT FUNDING SOURCES

This invention was partially made with government support under Pediatric Device Consortia Grant Program (PDC) awarded by the United States Food and Drug Administration.

BACKGROUND OF THE INVENTION

Field of the Art

The disclosure as detailed herein is in the technical field of medicine. More specifically, the present disclosure relates to the technical field of x-ray imaging. Even more specifically, the present disclosure relates to the technical field of medical software.

Discussion of the State of the Art

Modern medical facilities such as hospitals or emergency care facilities are often large and complex organizations. A medical facility may be organized into various departments or branches that specialize in a particular type of patient care or expertise. For example, a medical facility may have a radiology department that handles various medical imaging tasks such as computed tomography (CT) systems, X-ray systems (including both conventional and digital or digitized imaging systems), magnetic resonance imaging (MRI) systems, positron emission tomography (PET) systems, ultrasound systems, nuclear medicine systems, and the like. Such systems provide invaluable tools for identifying, diagnosing and treating physical conditions and greatly reduce the need for surgical diagnostic intervention. In many instances, these modalities complement one another and offer the physician a range of techniques for imaging particular types of tissue, organs, physiological systems, and so forth. However, patients requiring an X-ray, for example, must often be transported to the radiology department or even a separate and geographically distant imaging center. This can present additional delays, costs, and inconveniences to the patient and the practitioners.

Digital imaging systems are becoming increasingly widespread for producing digital data that can be reconstructed into useful radiographic images. In one application of a digital imaging system, radiation from a source is directed toward a subject, typically a patient in a medical diagnostic application, and a portion of the radiation passes through the subject and impacts a detector. The surface of the detector converts the radiation to light photons, which are sensed. The detector is divided into an array of discrete picture elements or pixels, and encodes output signals based upon the quantity or intensity of the radiation impacting each pixel region. Because the radiation intensity is altered as the radiation passes through the subject, the images reconstructed based upon the output signals may provide a projection of tissues and other features similar to those available through conventional photographic film techniques.

In use, the signals generated at the pixel locations of the detector are digitized. The digital values are transmitted to processing circuitry where they are filtered, scaled, and further processed to produce the image data set. The data set may then be used to reconstruct the resulting image, and display the image.

Despite advances in the art, there remain significant shortcomings in existing systems used for portable diagnostic imaging. Current mobile radiography/fluoroscopic imaging systems are cumbersome and expensive. These mobile systems normally incorporate a fixed, mechanical C-arm, or other mechanical configuration which connects the radiation source and the detector to one another, in order to mechanically fix the detector relative to the X-ray source to prevent misalignment outside of normally government-regulated, pre-determined tolerances. In addition, the spatial location of the detector is not always known relative to the X-ray source, as is the case in fixed, permanent digital radiography/fluoroscopic (DR) imaging systems. Especially when the subject to be imaged is very fragile or largely immobile, the need continues to exist for mobile systems which comply with applicable regulations.

SUMMARY OF THE INVENTION

The present invention is deemed to meet this need, amongst others, in a highly facile and effective way. In particular, the present invention provides a positioning system which enables users to continuously know the spatial location of the detector relative to the X-ray source. The X-ray source can more easily be aligned, and monitored for maintenance of alignment, with the portable detector within predetermined tolerances during procedures. In preferred embodiments, the invention further provides radiation interlock switch to prevent the emission of radiation if for whatever reason the X-ray source and detector are not aligned within the predetermine tolerance.

Thus, in one embodiment of this invention a mobile radiography/fluoroscopic imaging system is provided, comprising a portable radiation source operable to emit radiation in a single exposure (radiographic), pulse and or continuance (fluoroscopic) exposures, wherein the X-Ray source is adapted to move in all degrees of freedom; a portable detector operable to detect the radiation in single (radiographic), pulse and or continuance (fluoroscopic) emission from the radiation source, wherein the detector is adapted to move independently of the radiation source in all degrees of freedom; and wherein the systems includes a radiation source collimator positioning plate, a radiation source multi axis motion sensor and a computer to align the X-ray source to the detector; wherein the computer is in communication with the radiation source; and wherein the computer sends an activation signal to the radiation source to indicate when radiation may be emitted.

In a preferred embodiment, the radiation source collimator includes a positioning plate that is configured to block substantially all radiation except for one or more small alignment radiation beams to be emitted through the plate and strike the detector, the positioning plate has one or more small alignment holes, i.e. positioning apertures that extend through the plate and are sized and configured to insure that the lowest possible radiation dose is emitted and passed through the plate during the alignment process of the X-ray source to the detector. The size of each positioning aperture may vary, but in certain aspects of the invention will be no greater than about 1 millimeter in diameter, and in other aspects of the invention, the number of positioning apertures is preferably 4, a computer with software in communication with the detector which contains a pixel grid pattern of the location of the pixels, the computer programmed to calculate the position of the radiation source relative to the detector from data receive from the detector indicative of the locations of the pixels activated by the alignment radiation beams striking the detector after passing through the positioning plate. The computer generates icons that represent the calculated position of the radiation source and detector and visually display the icons on a visual display, such as an LCD or LED monitor, for example. The visual display is mounted on the radiation source which provides the operator a visual aid to align the radiation source to the detector. Immediately after a positioning radiation exposure has been initiated the radiation source collimator positioning plate and detector pixel grid pattern provide data which the computer process to calculate the present position and orientation of the radiation source relative to the detector. If the present position of the radiation source is not aligned to the detector, the radiation source or detector must be repositioned, a second exposure is initiated, the computer calculates the reposition location of the radiation source with respect to the detector, if the radiation source is not aligned to the detector, the radiation source or detector is repositioned and a third exposure is initiated. The operator will perform this process until the icons on the visual display are aligned. In one aspect of the invention where the radiation source and detector have the capability to produce pulses of continuance fluoroscopy, the operator can observe the icons on the visual display and align the radiation source to the detector by observing the icon on the visual display as the radiation source or detector are repositioned, the computer will update the new position of the radiation source or detector icon displayed on the visual display in real time as the radiation source or detector is repositioned. The operator would continue repositioning the radiation source or detector while observing the icons of the visual display until the icons are aligned. One can easily align the radiation source to the detector by moving the radiation source or detector until the icons displayed on the visual display representing the radiation source and detector are aligned to each other.

In one aspect of the invention, the radiation source collimator includes a positioning plate that is configured to block substantially all radiation except for one or more small alignment radiation beams to be emitted through respective aperture(s) extending through the plate so as to strike the detector, and the radiation source comprises one or more multi-axis motion sensors such as, for example: a KVH Industries Inc., model DSP-1760 three-axis fibre optic gyro, and the Murta Electronics model SCCA100T-D02-1 dual axis inclinometer, a computer with software in communication with the detector which contains a pixel grid pattern of the location of the pixels, the computer programmed to calculate the position of the radiation source relative to the detector from data receive from the detector indicative of the locations of the pixels activated by the small alignment radiation beams striking the detector after passing through the positioning plate.

The computer generated icons representing the radiation source and the detector are visually displayed on a visual display. The visual display is mounted on the radiation source to provide the operator a visual aid to align the radiation source to the detector. Immediately after a positioning radiation exposure has been initiated the radiation source collimator positioning plate and detector pixel grid pattern provide data which the computer processes to calculate the present position and orientation of the radiation source relative to the detector. If the present position of the radiation source with respect to the detector is not aligned to within a predetermine tolerance, the radiation source or detector must be repositioned. The computer is also in communication with the radiation source multi axis motion sensor. The computer communicates to the sensor the calculated position and orientation of the radiation source with respect to the detector. Movement of the radiation source is sensed by the sensor, the sensor transmits in real time the movement data, of the direction and axis to the computer, the received data is processed by the computer and in real time the computer updates the location of the radiation source icon on the visual display. One can easily align the radiation source to the detector by moving the radiation source until the icon displayed on the visual display representing the radiation source and detector are aligned to each other.

Advantageously, fewer radiation exposures are required to achieve alignment of the radiation source to the detector, and the radiation source multi axis motion sensor provides positioning data to align the radiation source to the detector after the initial radiation exposure.

In another embodiment the radiation source collimators internal shutters can be adjusted to only allow a small alignment radiation beam or one or more small holes can be placed in the internal shutters to allow only small alignment radiation beams to be emitted and strike the detector pixels, the activated pixels location can be calculated by the computer to align the X-ray source to the detector, and a computer with software in communication with the detector which contains a pixel grid pattern of the location of the pixels, the computer calculates the position of the x-ray source relative to the detector from data receive from the detector pertaining to the locations of the pixels activated by the small alignment radiation beams.

In yet another embodiment any object place between the radiation source and detector to prevent radiation from striking the detector, except for alignment radiation beams that will strike and activate certain detector pixels and send data to a computer to calculate the position, location, and orientation of the detector relative to the X-ray source.

In another embodiment, the alignment computer can be a dedicated alignment computer, a microprocessor/software processor, radiation source computer/software processor, detector computer/software processor, or any other computer/software processor that can be programmed to perform the calculation and positioning tasks.

In another embodiment, the radiation source multi-axis motion sensor can be any motion sensor device, such as for example: a KVH Industries Inc., model DSP-1760 three-axis fibre optic gyro, and the Murta Electronics model SCCA100T-D02-1 dual axis inclinometer, or other motion tracking device, such as for example, and inertial measuring units (IMU), fiber optic shape sensing, etc.

In yet another embodiment, data provided by the detector pixel grid pattern may not be easily accessible or available with some detectors. An alternative method to determine position of the detector relative to the radiation source can be accomplished. Immediately after a positioning radiation exposure has been initiated a radiographic image is produced displaying small white dots representing the pixels activated by the radiation source positioning plate apertures. The computer software can be programmed to calculate the location of the white dots relative to the detector geometric size, shape and distance from the radiation source. The computer can then calculate present position and orientation of the radiation source relative to the detector.

In a further embodiment, the radiation source is prevented from emission of radiation until the detector and the radiation source have achieved predetermined alignment conditions.

In another embodiment, emission of radiation from the radiation source is automatically performed upon and during achievement of predetermined alignment conditions between the detector and the radiation source.

Preferably, the radiation source is capable of emitting radiation in a single emission and in pulsed or continuance emissions.

The invention may further include an indicator adapted to notify an operator when the detector and the radiation source have achieved predetermined alignment conditions, wherein the indicator is a visible indicator or an audible indicator.

In a further embodiment, the indicator is adapted to notify an operator when the detector is within a predetermined range of the radiation source.

In a more preferred embodiment, the detector is a portable flat panel digital X-ray detector.

Preferably, the computer includes software adapted to receive position and orientation signals from the detector of the activated pixels by the small alignment radiation beam produced by the X-ray source collimator positioning plate.

Yet another embodiment of the invention provides an improvement to a fluoroscopic medical procedure which sends radiation from a radiation source through a subject in order to produce radiological images of the subject, the improvement comprising placing the subject between a portable detector and the radiation source, the portable detector being operable to detect radiation from the radiation source, wherein the detector and the radiation source are each adapted to move independent of one another and to move in all degrees of freedom, and the radiation source contains a positioning plate, to provide small positioning radiation beams to activate detector pixels, a computer in communication with the detector pixel grid pattern detects which pixel or pixels the small alignment radiation beams strikes and establish the position, distance and orientation of the radiation source and the detector, and so as to send an activation signal to the radiation source to indicate when radiation may be emitted.

In another embodiment, the aforesaid improvement further comprises automatically preventing the radiation source from emitting radiation until the detector and the radiation source have achieved one or more predetermined alignment conditions.

Yet another embodiment of the aforesaid improvement further comprising automatically triggering the emission of radiation from the radiation source upon and during achievement of one or more predetermined alignment conditions between the detector and the radiation source.

These and still other embodiments, features and advantages of the invention will now become even more apparent from the accompanying figures, detailed description and claims.

BRIEF DESCRIPTION OF THE DRAWING FIGURES

The accompanying drawings illustrate several embodiments of the invention and, together with the description, serve to explain the principles of the invention according to the embodiments. It will be appreciated by one skilled in the art that the particular embodiments illustrated in the drawings are merely exemplary, and are not to be considered as limiting of the scope of the invention or the claims herein in any way.

DETAILED DESCRIPTION

Figure 1:
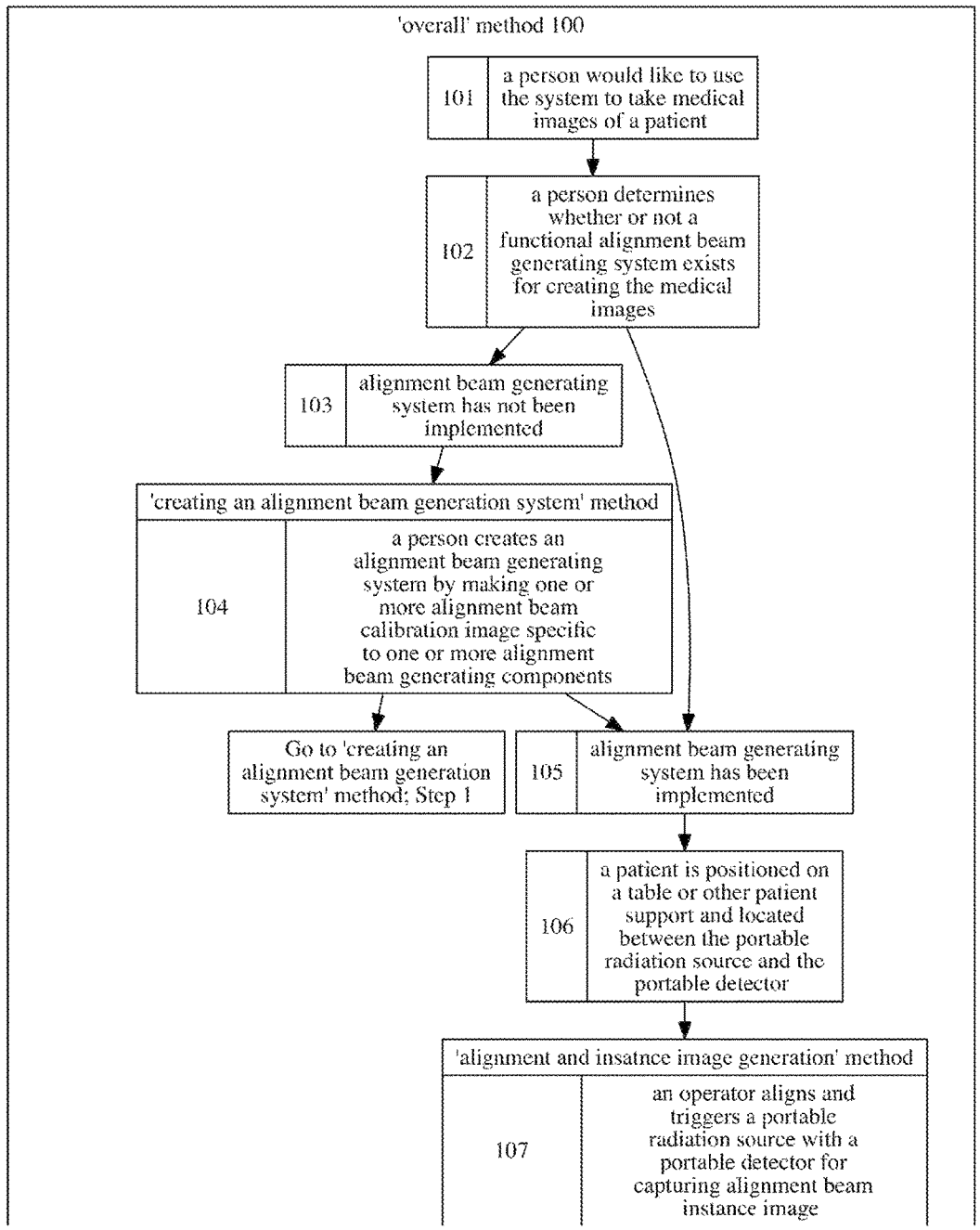
FIG. 1 is a top partial diagram view which shows overall use of the device.

One or more different inventions may be described in the present application. Further, for one or more of the inventions described herein, numerous alternative embodiments may be described; it should be appreciated that these are presented for illustrative purposes only and are not limiting of the inventions contained herein or the claims presented herein in any way. One or more of the inventions may be widely applicable to numerous embodiments, as may be readily apparent from the disclosure. In general, embodiments are described in sufficient detail to enable those skilled in the art to practice one or more of the inventions, and it should be appreciated that other embodiments may be utilized and that structural, logical, software, electrical and other changes may be made without departing from the scope of the particular inventions. Accordingly, one skilled in the art will recognize that one or more of the inventions may be practiced with various modifications and alterations. Particular features of one or more of the inventions described herein may be described with reference to one or more particular embodiments or figures that form a part of the present disclosure, and in which are shown, by way of illustration, specific embodiments of one or more of the inventions. It should be appreciated, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Headings of sections provided in this patent application and the title of this patent application are for convenience only, and are not to be taken as limiting the disclosure in any way.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Devices that are in communication with each other need not be in continuous communication with each other, unless expressly specified otherwise. In addition, devices that are in communication with each other may communicate directly or indirectly through one or more communication means or intermediaries, logical or physical.

A description of an embodiment with several components in communication with each other does not imply that all such components are required. To the contrary, a variety of optional components may be described to illustrate a wide variety of possible embodiments of one or more of the inventions and in order to more fully illustrate one or more aspects of the inventions. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the invention(s), and does not imply that the illustrated process is preferred. Also, steps are generally described once per embodiment, but this does not mean they must occur once, or that they may only occur once each time a process, method, or algorithm is carried out or executed. Some steps may be omitted in some embodiments or some occurrences, or some steps may be executed more than once in a given embodiment or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments of one or more of the inventions need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of embodiments of the present invention in which, for example, functions may be executed out of order from that shown or discussed, including substantially concurrently or in reverse order, depending on the functionality involved, as would be understood by those having ordinary skill in the art.

A preferred embodiment of the present invention is now described with reference to the figures, where like reference numbers indicate identical or functionally similar elements. Also in the figures, the leftmost digit of each reference number corresponds to the figure in which the reference number is first used. While specific configurations and arrangements are discussed, it should be understood that this done for illustrative purposes only. A person of ordinary skill in the relevant art will recognize that other configurations and arrangements can be used without departing from the spirit and scope of the invention. It will be apparent to a person of ordinary skill in the relevant art that this invention can also be employed in a variety of other systems and applications.

Figure 9:
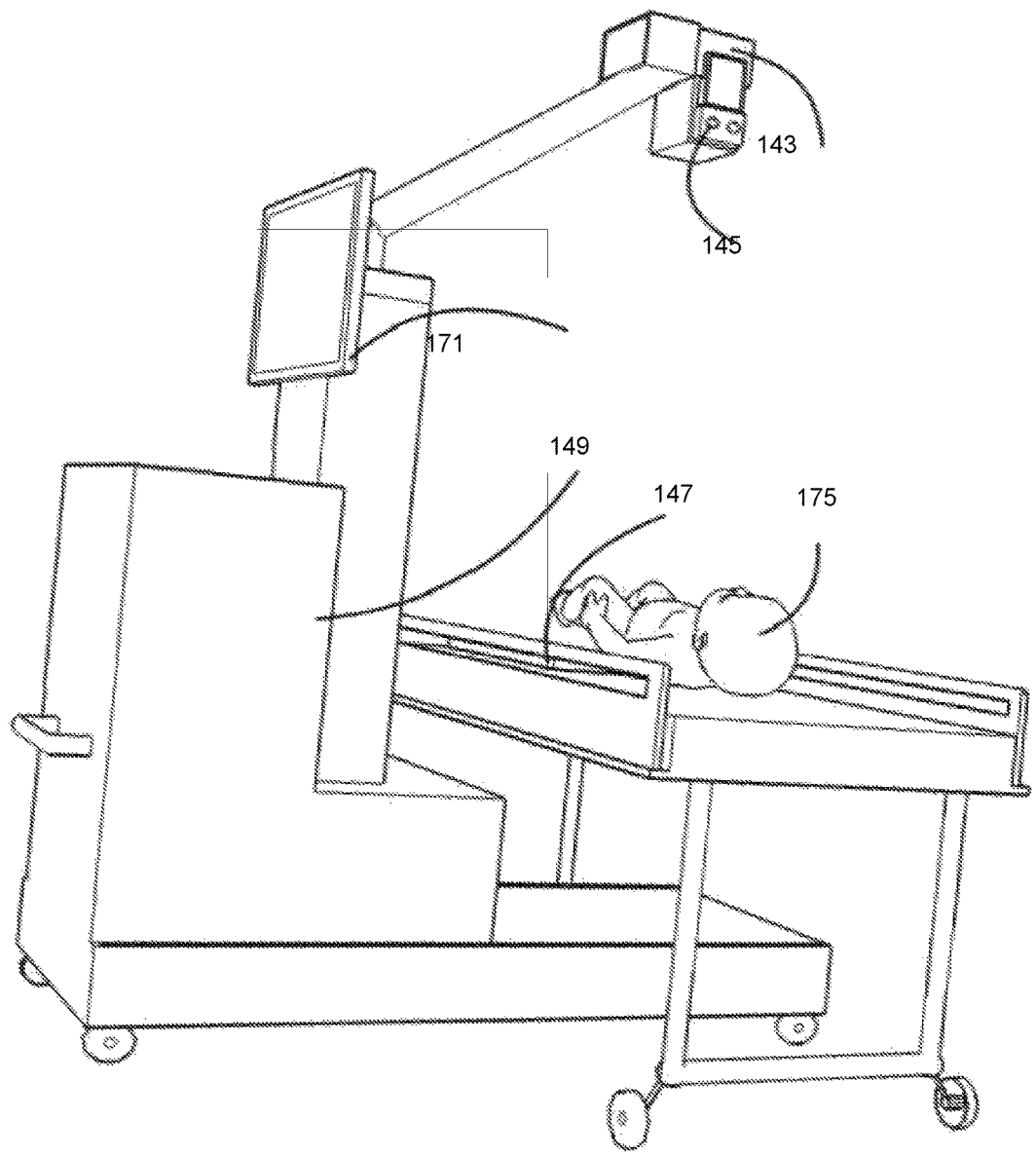
FIG. 9 is a perspective view which shows the radiation source system for imaging a patient.
Figure 10:
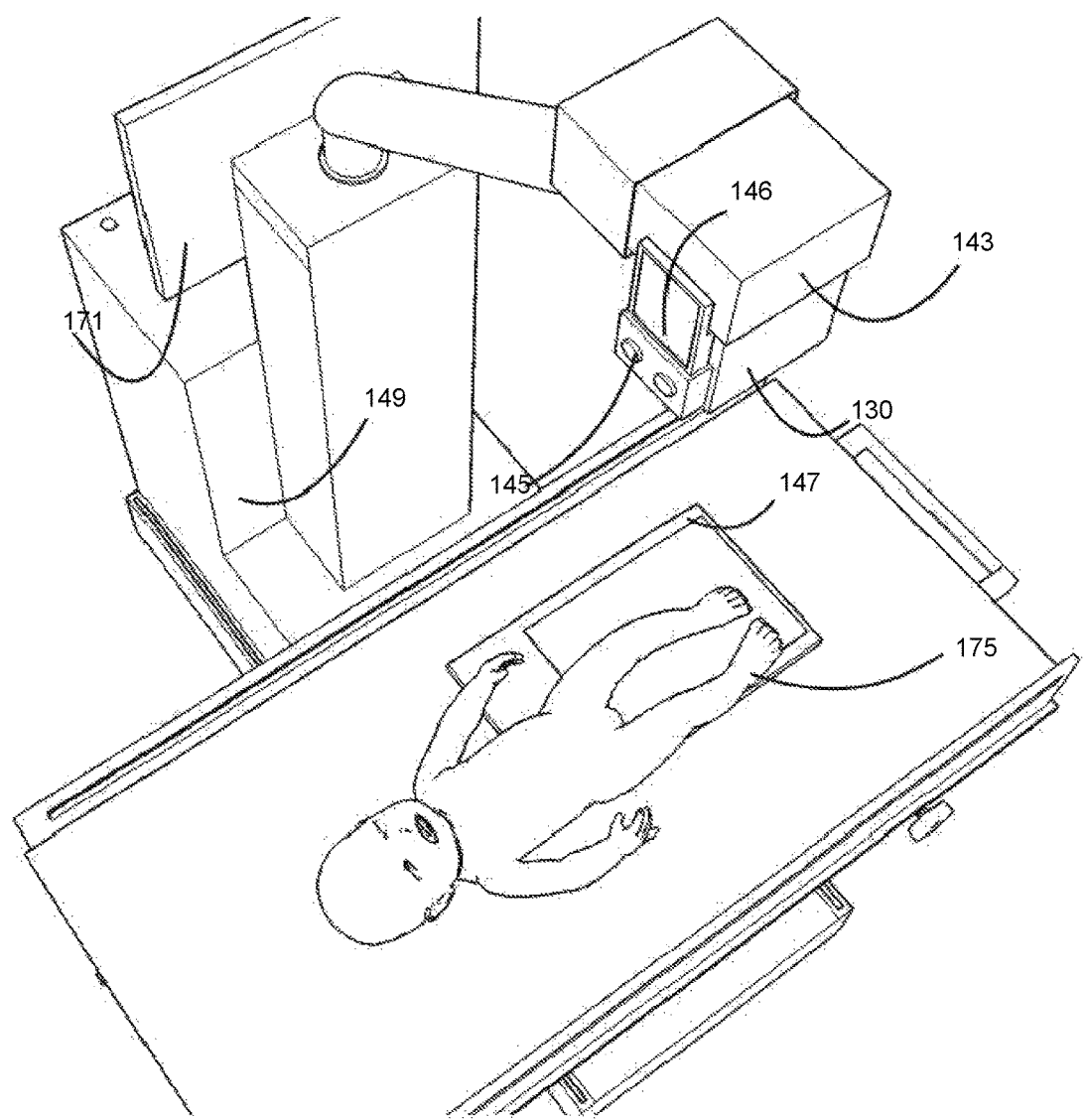
FIG. 10 is a perspective view which shows the radiation source for imaging a patient aligned with a portable detector for an instance image.
Figure 22:
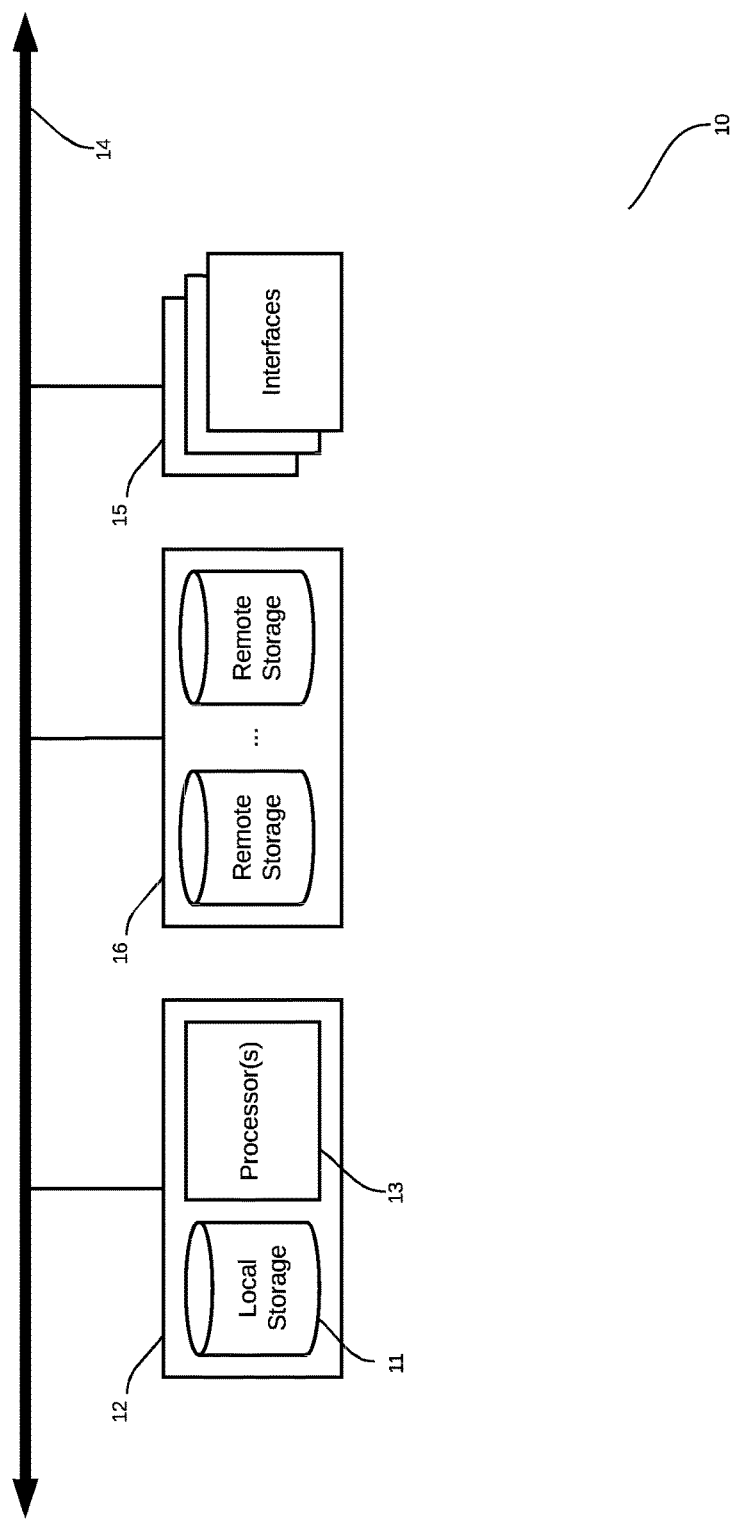
FIG. 22 is a block diagram illustrating an exemplary hardware architecture of a computing device used in an embodiment of the invention.

The invention has some elements that are commonly known and some specifically defined terms including: a patient 175 (referring to FIGS. 9 and 10), an operator, APR, predetermined tolerance, software, a database (for example, local storage 11 and remote storage 16, referring to FIG. 22), user input, a user device 24 (referring to FIG. 23), a user interface, a networks 31, 54, a server 32 (referring to FIGS. 24 and 25), a computer 171 (referring to FIGS. 9, 10, 13, 14, 15, and 16) a central processing unit, memory (such as memory 25 referring to FIG. 23), an operating system, a graphical user interface, a presentation layer 27 (referring to FIG. 23), one or more modules, and finally a plurality of program code. However, their use and relationships to the novel components and steps of the invention render them applicable herein. In order to preface the roles that they play in the specification, they are subsequently explained here.

The term user input may comprise text or information that is input by the user into one or more modules presentation layer 27. The user device 24 (referring to FIG. 23) comprises an interactive device that has one or more CPUs (for example, processor 13 referring to FIG. 22 and processors 21 referring to FIG. 23) and memory 25 with one or more modules containing executable instructions, typically a computer 171. The term user interface comprises a display mechanism for a graphical user interface which in turn is part of the presentation layer 27 of one or more modules. In some embodiments, it is thought that examples of a user interface may include: a screen, a display, a projector, a touch panel, a pointing device, a scrolling device, a button, or a switch.

The term network 31 may comprise a communications network that allows computers to exchange data. In some embodiments, it is thought that examples of a network 31 may include: a personal area network, a wireless personal area network, a near-me area network, a local area network, a wireless local area network, a wireless mesh network, a wireless metropolitan area network, a wireless wide area network, a cellular network, a home area network, a storage area network, a campus area network, a backbone area network, a metropolitan area network, a wide area network, an enterprise private network, a virtual private network, an intranet, an extranet, an internetwork, an internet, near field communications, or a mobile telephone network.

The term server 32 may comprise a system (for example, programming instructions operating suitable computer hardware) that responds to requests across a computer network and has one or more CPUs (for example, processor 13 referring to FIG. 22 and processors 21 referring to FIG. 23) capable of executing one or more instructions on one or modules present on memory 25. The term computer 171 comprises a general-purpose device that can be programmed to carry out a finite set of arithmetic or logical operations. In some embodiments, it is thought that examples of a computer 171 may include: desktop computers, carputers, game consoles, laptops, notebooks, a palmtop, a tablet, smartphones, or smartbooks. The computer 171 preferably comprises a central processing unit, a memory, an operating system, and finally a graphical user interface.

The term central processing unit comprises hardware within a computer that carries out the instructions of a computer program by performing the basic arithmetical, logical, and input/output operations of the system. The term memory comprises the physical devices used to store programs (sequences of instructions) or data (e.g. program state information) on a temporary or permanent basis for use in a computer or other digital electronic device.

The term operating system comprises a collection of software that manages computer hardware resources and provides common services for computer programs. The term graphical user interface comprises a type of user interface that allows users to interact with electronic devices through graphical icons and visual indicators such as secondary notation, as opposed to text-based interfaces, typed command labels or text navigation.

The term presentation layer 27 comprises graphical output from one or more modules for user interaction typically one or more graphical user interface. I some embodiment, the term module as used herein may comprise a block of programming instructions hosted on memory 25 executed by the one or more CPUs which perform one or more series of functions. The term program comprises a sequence of instructions, written to perform a specified task with a computer that is executed by the one or more CPUs.

Referring now to FIG. 1, in some embodiments, the use of the instant invention is as disclosed: First, a person, be it an operator, or other personnel, would like to use the instant invention to take medical images or video of a patient 175 (Step 101). The patient 175 comprises any recipient of health care services who is the subject of use of the instance invention. In some embodiments, it is thought that examples of a patient 175 may include: an outpatient, an inpatient, or a day patient. An operator comprises an individual who provides preventive, curative, promotional or rehabilitative health care services with training capable of using the instance system. In some embodiments, it is thought that examples of an operator may include: an athletic trainer, an audiologist, a chiropractor, a clinical nurse specialist, a clinical officer, a community health worker, a dentist, a dietitian and nutritionist, an emergency medical technician, a feldsher, a health administrator, a medical assistant, a medical laboratory scientist, a midwife, a nurse anesthetist, a nurse, a paramedic, a pharmacist, a pharmaconomist, a pharmacy technician, a phlebotomist, a physician, a physician assistant, a podiatrist, a psychologist, a psychotherapist, a physical therapist (physiotherapist), a radiographer, a radiotherapist, a respiratory therapist, a speech-language pathologist, a surgeon, a surgeon's assistant, or a surgical technologist.

Next, a person determines whether or not a functional alignment beam calibration system 139 exists for creating the medical images (Step 102). If alignment beam calibration system 139 has not been implemented (Step 103), then a person creates an alignment beam calibration system 139 by making one or more alignment beam calibration image 134 specific to one or more alignment beam generating components 130 (Step 104). The alignment beam calibration system 139 is a configuration of components that allows an operator to compare an alignment instance image 137 with an alignment beam calibration image 134.

Figure 3:
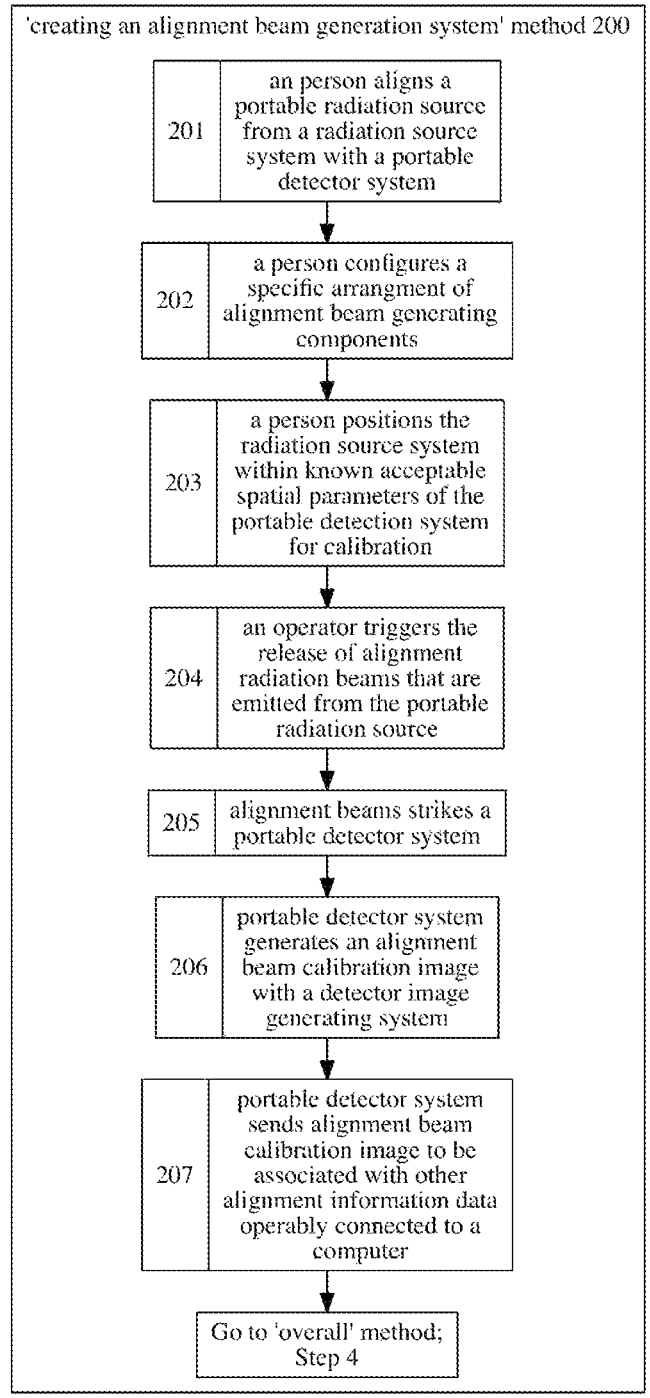
FIG. 3 is a diagram view which shows creating a calibration system.

Referring now to FIG. 3, in order to create the calibration, a person aligns a portable radiation source 143 from a radiation source system 149 with a portable detector system 147 (Step 201). The portable radiation source 143 comprises a device used to generate x-rays used by one or operator to acquire an x-ray image of the inside of an object that can also be can used for the common x-ray uses including sterilization, fluorescence, medical and diagnostic purposes. Typically, it would allow one to take images or video from many degrees of freedom for use with a portable detector. In some embodiments, it is thought that an example of a portable radiation source 143 could be a single pulse or continuous emission source, and the like.

The portable radiation source 143 is typically part of a radiation source system 149. A radiation source system 149 comprises the components and controls of an x-ray system that allows the portable radiation source 143 to be used effectively in practice. In some embodiments, it is thought that examples of a radiation source system 149 may include: a computer, x-ray software, a portable cart, caster wheels, or articulating arms.

The portable detector system 147, which receives x-rays, comprises a component (not attached to a radiation source system 149, but freely movable) that convert the X-ray photons received on its surface to lower energy photons, and subsequently to electric signals, which are acquired and processed to reconstruct an image of the features within the patient.

Next in order to create the calibration, a person configures a specific arrangement of alignment beam generating components 130 (Step 202). The alignment beam generating components 130 comprises one or more components embedded or added to the radiation system in order to generate an alignment radiation beams 141. In some embodiments, the alignment beam generating components 130 may preferably comprise a positioning plate 158, a collimator 167, a positioning aperture 155, and/or beam variation components. These components may generate an alignment radiation beam.

In some embodiments, a collimator 167 comprises a device that adjusts a beam size to a desired size for imaging a desired area. The collimator 167 may preferably comprise collimator shutter blades 144. These function as part of the collimator 167 that allow narrowing of the radiation beam that can function to create an alignment beam aperture, and/or narrow the beam for other imaging purposes In some embodiments, one or more positioning plate 158 comprises one or more configurable plates between the portable radiation source 143 and the portable detector system 147. Positioning plate 158 block most radiation except for the positioning aperture which constrains the beams to form an alignment beam. In some embodiments, a positioning aperture 155 is created. A positioning aperture 155 comprises an aperture that is the remaining efflux of radiation, after radiation passes through the alignment beam generating components 130.

In addition, the alignment beam generating components 130 has multiple alternative embodiments herein termed the "collimator hole in shutter blades" embodiment, the "incomplete closed collimator" embodiment, the "positioning aperture plate" embodiment, and the "low dose system" embodiment.

The "collimator hole in shutter blades" embodiment comprises an embodiment where the collimator has holes in the shutter blades that are the source of the radiation alignment radiation beams 141. The "incomplete closed collimator" embodiment comprises an embodiment where the collimator does not have holes in the shutter blades, but rather generates an alignment radiation beams 141 by having an incomplete closure of the collimator shutter blades 144.

The "positioning aperture plate" embodiment comprises one or more configurable plates that serves to limit most or all exit radiation from the radiation source, except for those through the alignment beam holes, thereby generating a radiation alignment radiation beams 141. The "low dose system" comprises an embodiment where the alignment radiation beams 141 are created by a portable radiation system capable of emitting a low dose alignment radiation beam.

Next, a person positions the radiation source system 149 within known acceptable spatial parameters of the portable detector system 147 for calibration (Step 203). Then, an operator triggers the release of alignment radiation beams 141 that are emitted from the portable radiation source (Step 204). The alignment radiation beams 141 comprises the radiation that is comes through one or more positioning aperture 155 that are used for aligning the portable radiation source 143 and the portable detector system 147.

Next, alignment beams strike a portable detector system 147 (Step 205). Then, the portable detector system 147 generates an alignment beam calibration image 134 with a detector image generating system 135 (Step 206). The detector image generating system 135 comprises a system preferably within the portable detector, that converts radiation beams from a portable radiation source 143 into an image (or in some embodiments, video with video frames as images) that can be analyzed by a computer. The detector image generating system 135 creates the alignment beam calibration image 134 and communicates that to the computer 171 via the communication unit 127. In other future steps, this mechanism also creates the alignment beam instance image 137, and a patient radiographic image.

The alignment beam calibration image 134 comprises an image that is specific to the choice of alignment beam generating components 130 type, wherein the image (which may be a frame from a video in some embodiments) is used to ascertain the alignment of the source and detector so an operator may reposition if out of alignment.

The communication unit 127 comprises a means for transmitting data from the detector to the computer. In some embodiments, it is thought that examples of communication unit 127 may include: Wi-Fi, Bluetooth™, a serial cable, an HDMI cable, or network means, and like.

In some embodiments, the calibration may be complete when the portable detector system 147 sends alignment beam calibration image 134 to be associated with other alignment information data 140 operably connected to a computer (Step 207). The alignment information data 140 comprises the data that comprises an instance of an alignment beam calibration system 139. Such as an alignment beam calibration image 134, an alignment beam instance image 137 or other data processed by the image processing system 151. In some embodiments, the person creating the calibration may be a person manufacturing the system at a factory, where in the calibration data is subsequently stored in memory on the system for consumer use.

Referring now to FIG. 1, once the alignment beam calibration system 139 has been implemented (Step 105), a patient 175 is positioned on a table or other patient support and located between the portable radiation source 143 and the portable detector system 147 (Step 106). Then as described in Steps 301-308 below in more detail: an operator aligns and triggers a portable radiation source 143 with a portable detector system 147 for capturing an alignment beam instance image 137 (Step 107).

Figure 4:
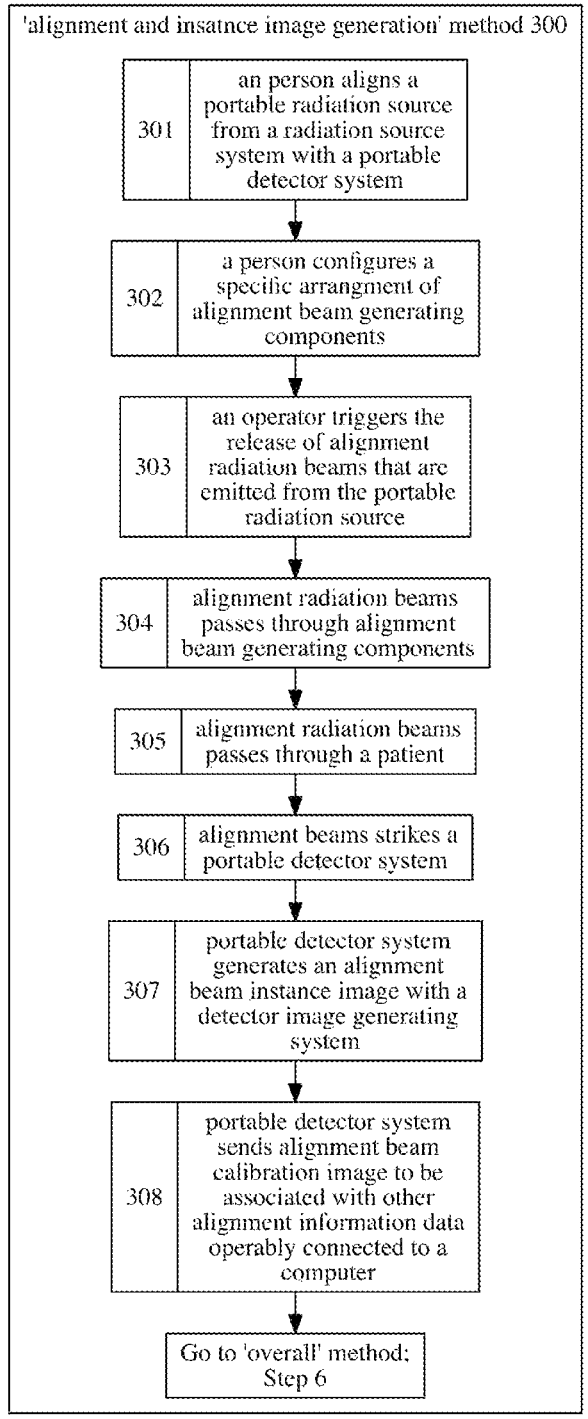
FIG. 4 is a diagram view which shows the method for alignment and instance image generation.

Referring now to FIG. 4, a person then configures a specific arrangement of alignment beam generating components 130 (Step 302). Next, an operator triggers the release of alignment radiation beams 141 that are emitted from the portable radiation source 143 (Step 303). Then, alignment radiation beams 141 passes through alignment beam generating components 130 (Step 304). Then alignment radiation beams 141 passes through a patient 175 (Step 305). Next, the alignment beams strike a portable detector system 147 (Step 306)

Figure 2:
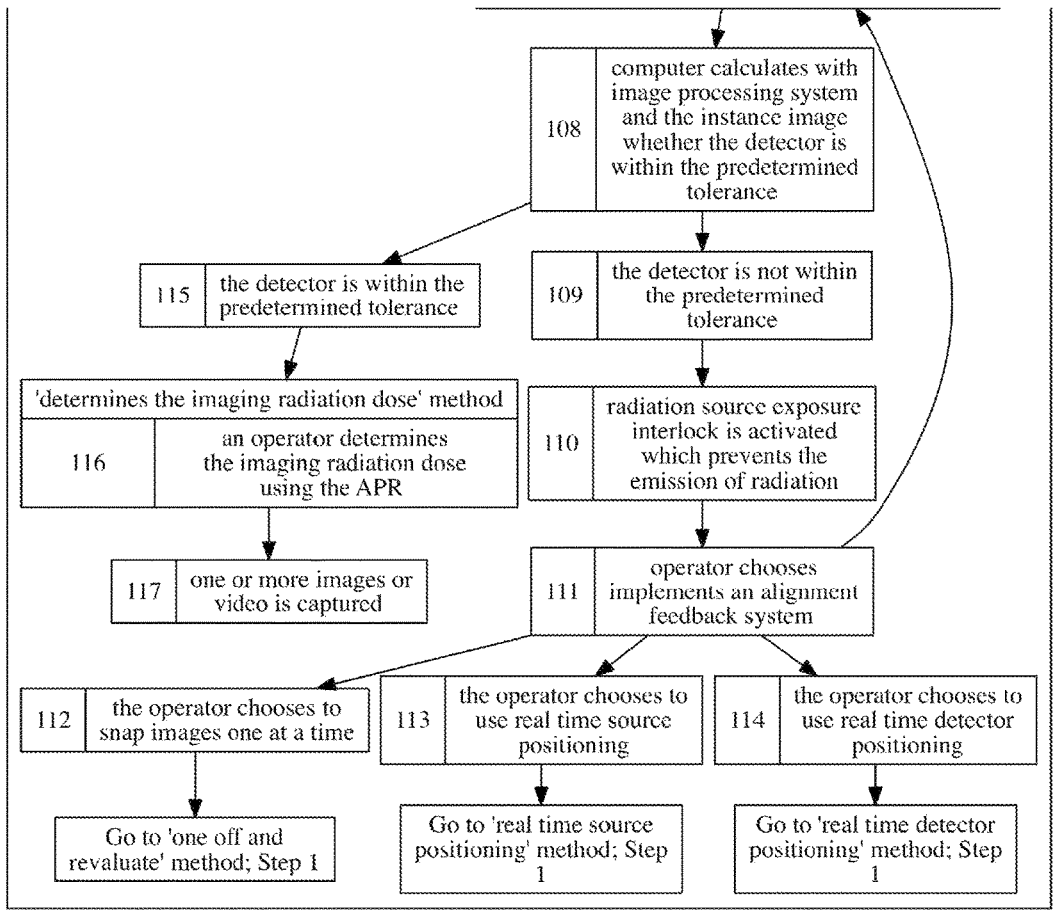
FIG. 2 is a bottom partial diagram view which shows overall use of the device.

Then, a portable detector system 147 generates an alignment beam instance image 137 with a detector image generating system 135 (Step 307). Next a portable detector system 147 sends alignment beam calibration image 134 to be associated with other alignment information data 140 operably connected to a computer (Step 308). Referring now to FIG. 2, subsequently, a computer calculates with image processing system 151 and the instance image whether the detector is within the predetermined tolerance (Step 108)

After comparison of the two images, if the detector is not within the predetermined tolerance (Step 109). Then a radiation source exposure interlock 132 is activated through a safety system 164 which prevents the emission of radiation (Step 110).

Figure 17:
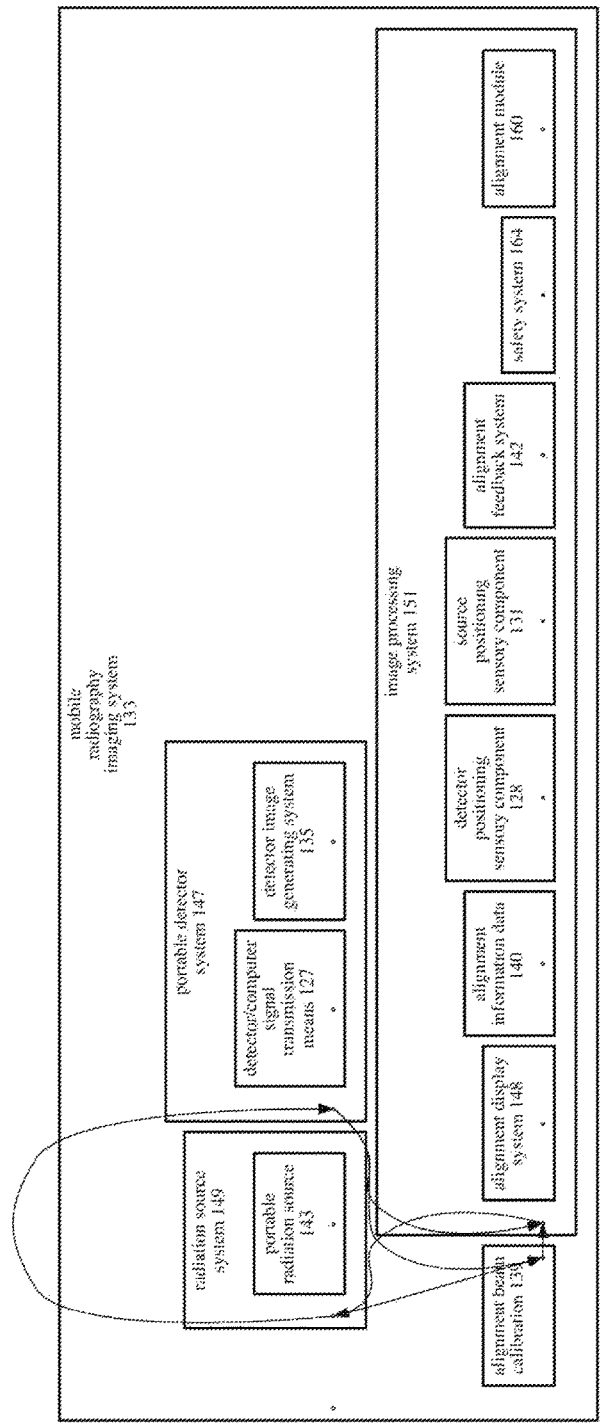
FIG. 17 is a diagram view which shows relationships between devices and modules.
Figure 21:
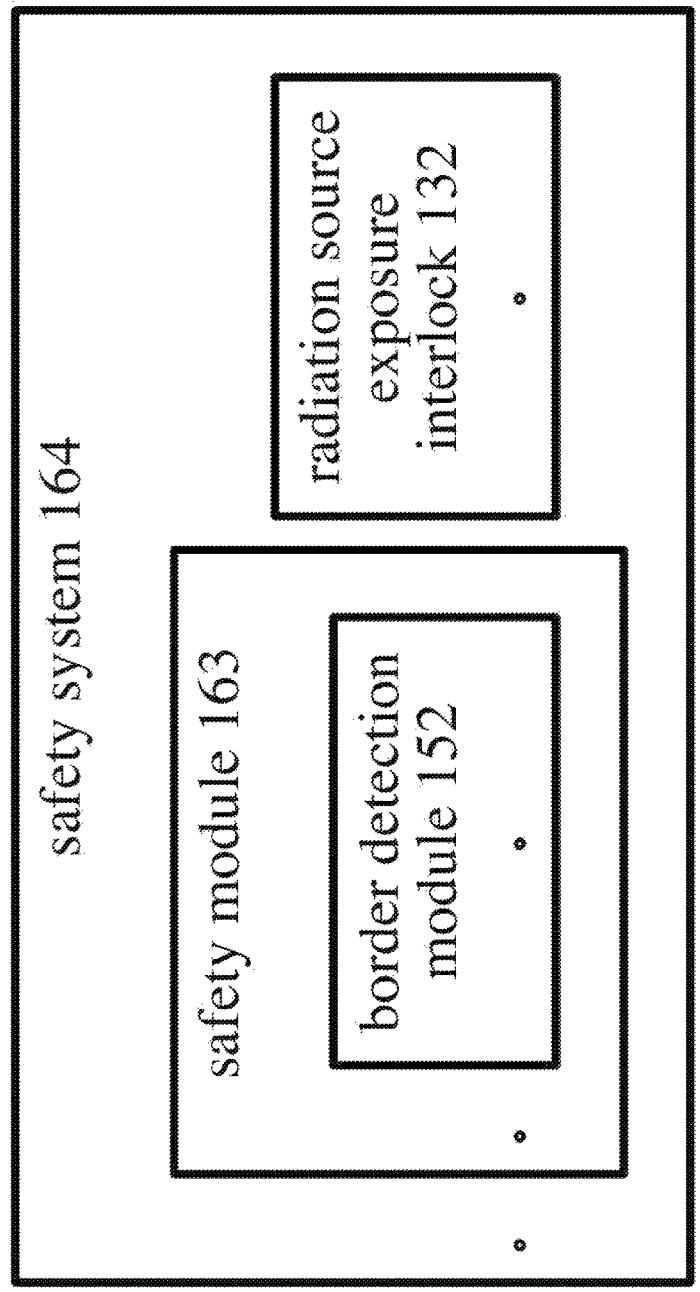
FIG. 21 is a diagram view which shows safety system and it sub modules.

Referring now to FIGS. 17 and 21, the safety system 164 comprises a system primarily concerned with using calibration image/instance images to implement safety functions and also preferably comprises the radiation source exposure interlock 132 and the safety module 163. The radiation source exposure interlock 132 comprises a programmatic and/or physical means that is capable of immediately shutdown and or prevent the initiation of x-rays from the radiation source. In some embodiments, this may occur through inhibition of existing signal. Preferably, the interlock provides a tonic inhibition of one or more imaging signal. Thus, when the predetermined tolerance threshold his achieved, imaging is activated through disinhibition of the interlock, and imaging is initiated. During imaging if measurement, such as (video frames from video) indicate that alignment is off, the interlock would again be engaged, preventing imaging. The safety module 163 comprises a module that is used primarily for implementing safety protocols such as shutdown or interlock and also preferably comprises the border detection module 152.

The border detection module 152 comprises a module that determines whether the position of the pixels from the instance image indicate that alignment radiation beams are approaching the outside of the detector. For example, the image may have a one-inch border width (though this may be in a predefined range), wherein if the alignment beam strikes within this region, it would indicate misalignment and engage the interlock.

Figure 5:
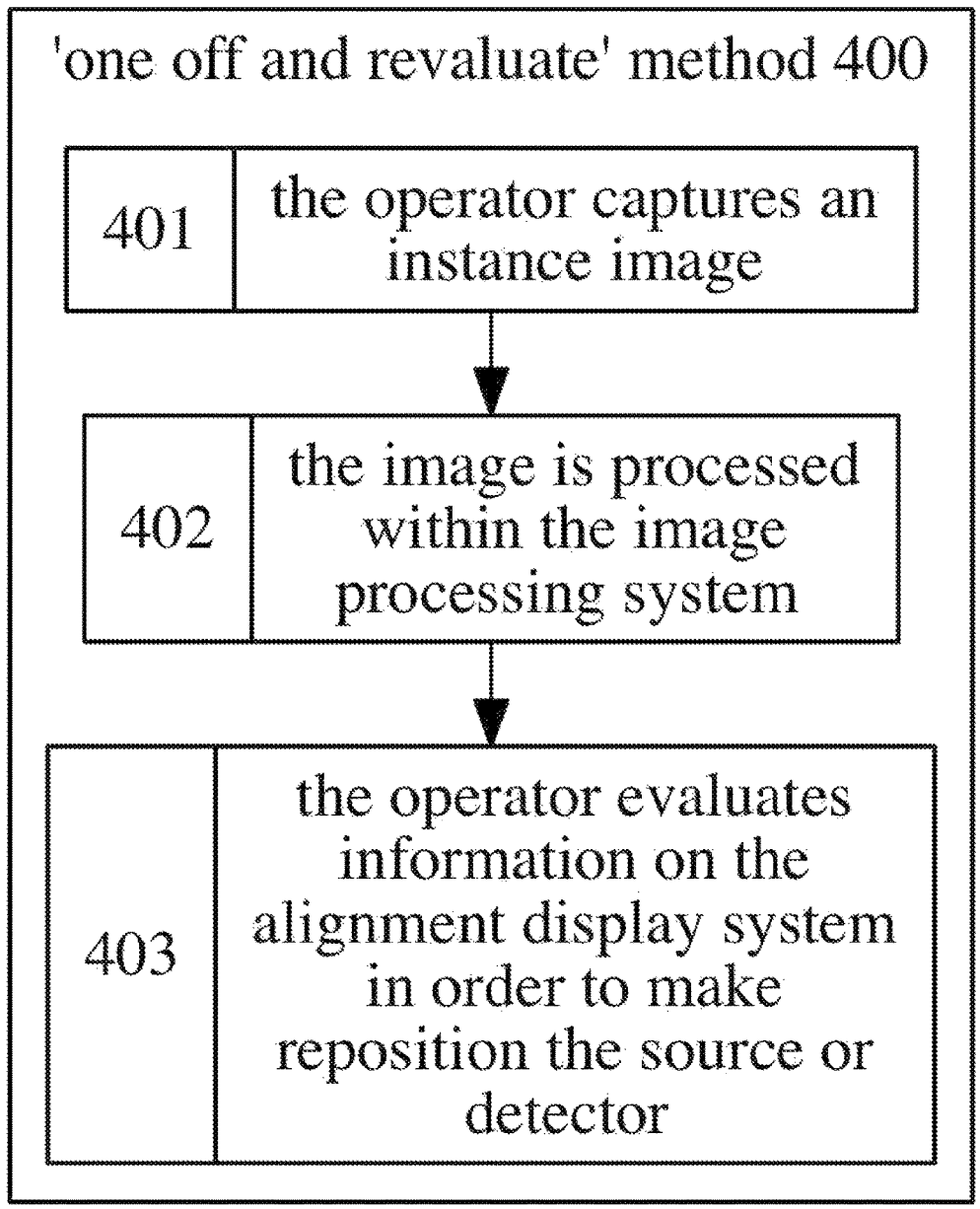
FIG. 5 is a diagram view which shows one-off and revaluate method of repositioning.

Referring now to FIG. 2, after the safety featured are executed, at this point an operator implements an alignment feedback system 142 (Step 111) in order to align the detector and the source. Example embodiments of methods used include: First, choosing to snap images one at a time and repositioning the detector or source (Step 112) as follows: Referring now to FIG. 5, the operator captures an instance image (Step 401) Next, the image is processed within the image processing system 151 (Step 402). Next, the operator evaluates information on the alignment display system 148 in order to make reposition the source or detector (Step 403).

Figure 6:
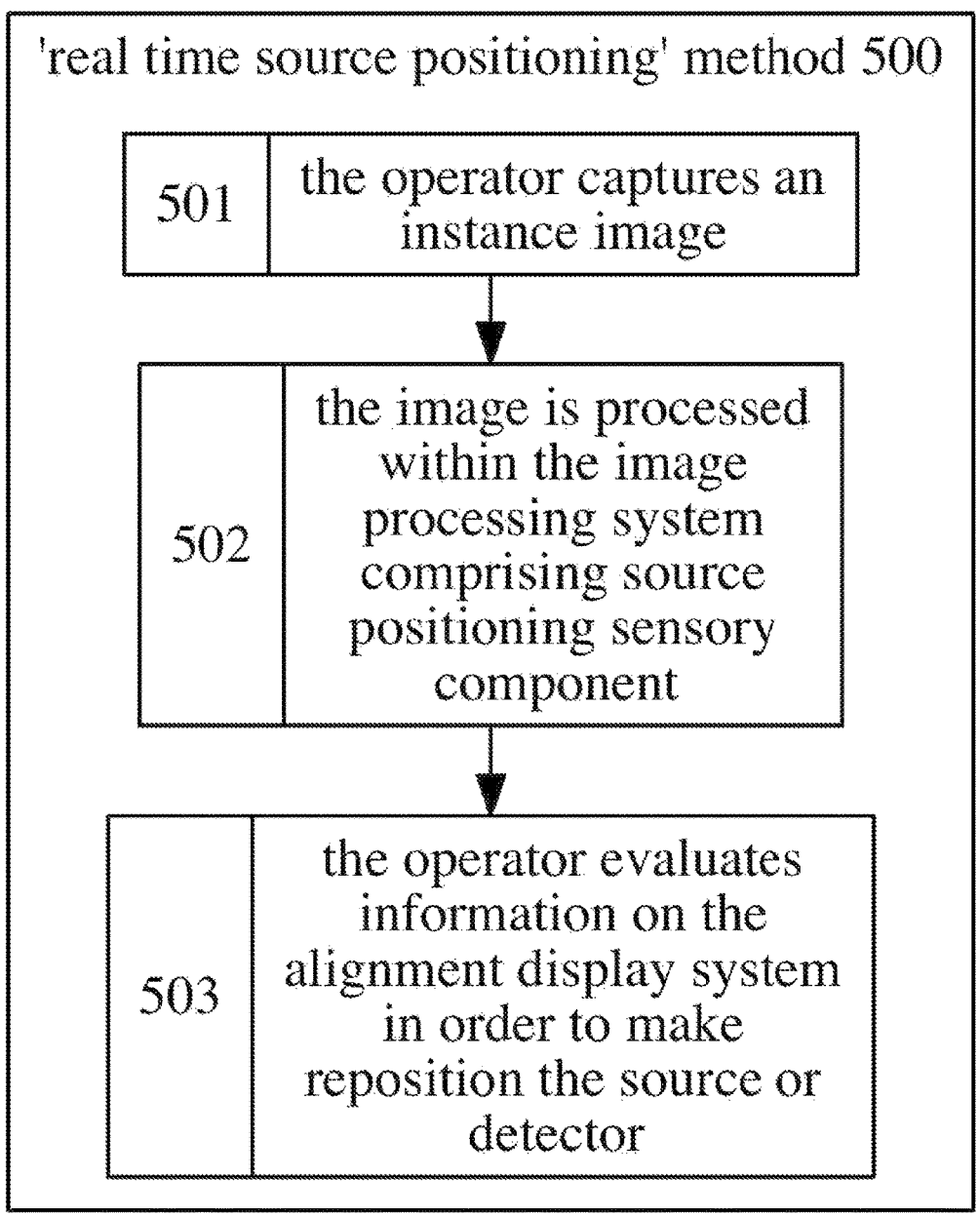
FIG. 6 is a diagram view which shows real-time source method of repositioning.

Referring now to FIG. 2, second, choosing to use real time source positioning (Step 113) as follows: Referring now to FIG. 6, the operator captures an instance image (Step 501). Next, the image is processed within the image processing system 151 comprising source positioning sensory component 131 (Step 502). Next, the operator evaluates information on the alignment display system 148 in order to make reposition the source or detector (Step 503).

Figure 7:
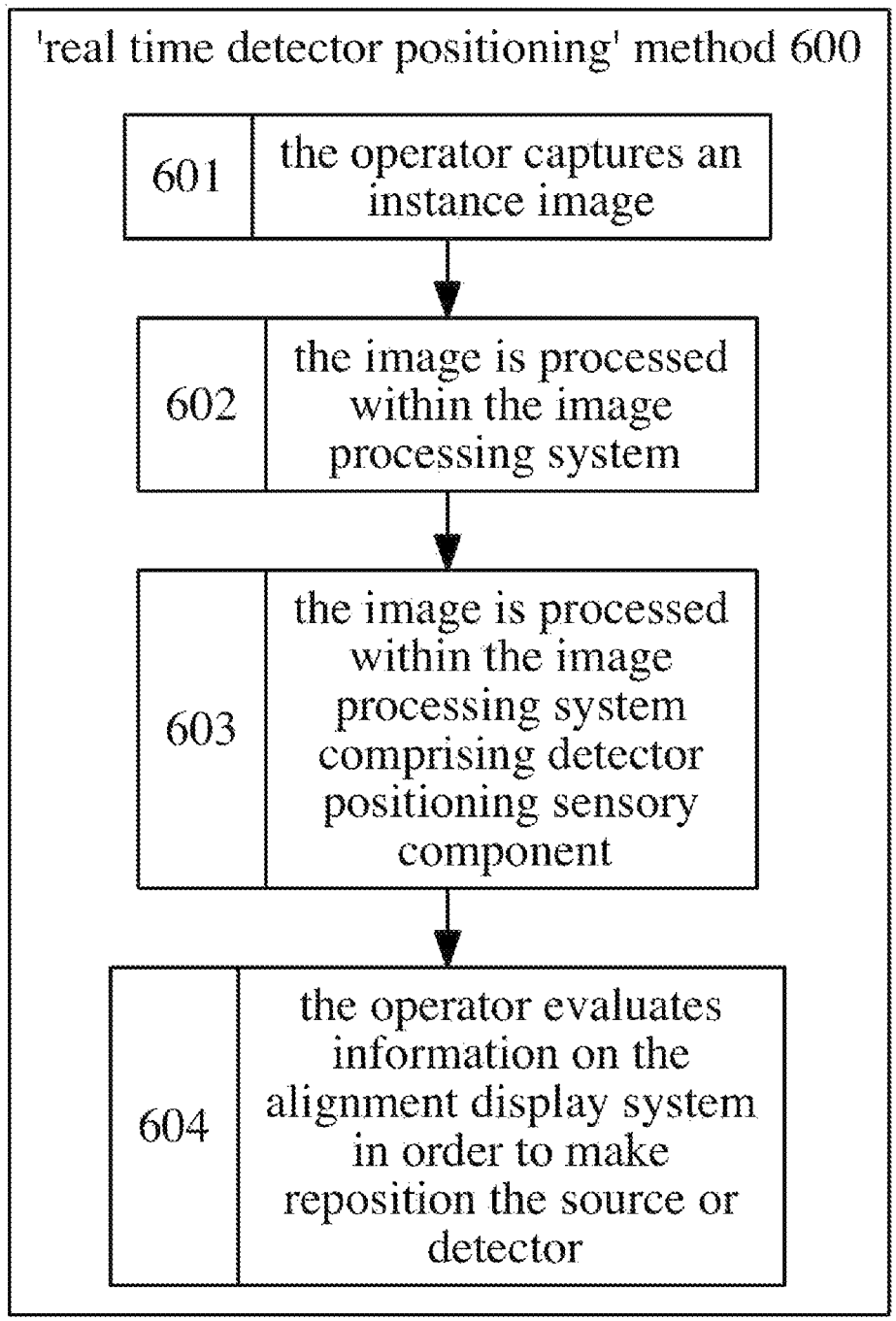
FIG. 7 is a diagram view which shows real-time detector method of repositioning.

Referring now to FIG. 2, third, choosing to use real time detector positioning (Step 114), as follows: Referring now to FIG. 7, the operator captures an instance image (Step 601).

Next, the image is processed within the image processing system 151 (Step 602). Next, the image is processed within the image processing system 151 comprising detector positioning sensory component 128 (Step 603). Next, the operator evaluates information on the alignment display system 148 in order to make reposition the source or detector (Step 604). Some embodiments of an alignment feedback system 142 may include auto-alignment. This an embodiment where if the radiation source system has motorized articulating components, it may coordinate alignment data for auto-alignment.

Figure 18:
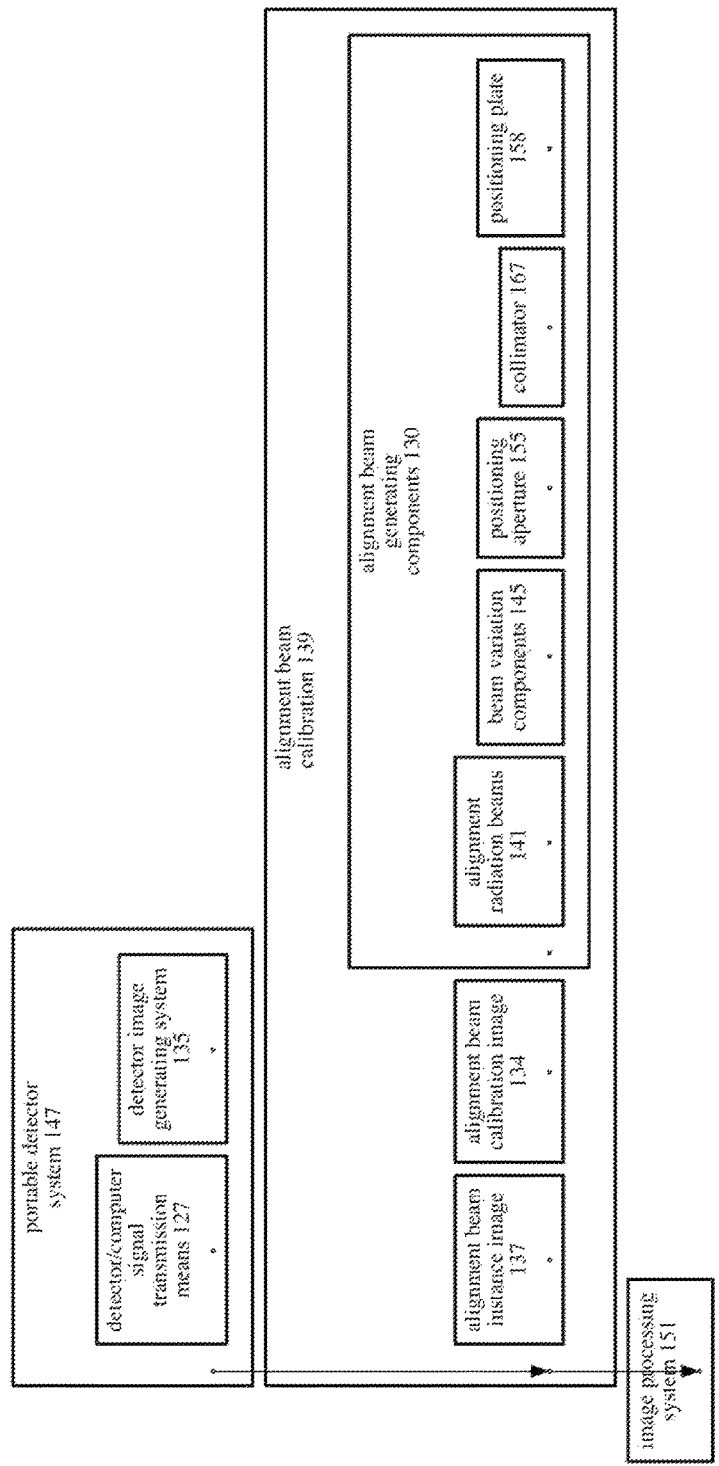
FIG. 18 is a diagram view which shows relationships between the alignment beam calibration system and the other systems.

In order to enact these methods, some embodiments include the following components. Referring now to FIGS. 17 and 18, the image processing system 151 comprises one or more modules on a computer that accept data from the alignment beam calibration system 139 and then relay positional information, relative to the radiation source. The image processing system 151 preferably comprises an alignment module 160, a safety system 164, an alignment feedback system 142, a source positioning sensory component 131, a detector positioning sensory component 128, an alignment information data 140, and finally an alignment display system 148.

Figure 19:
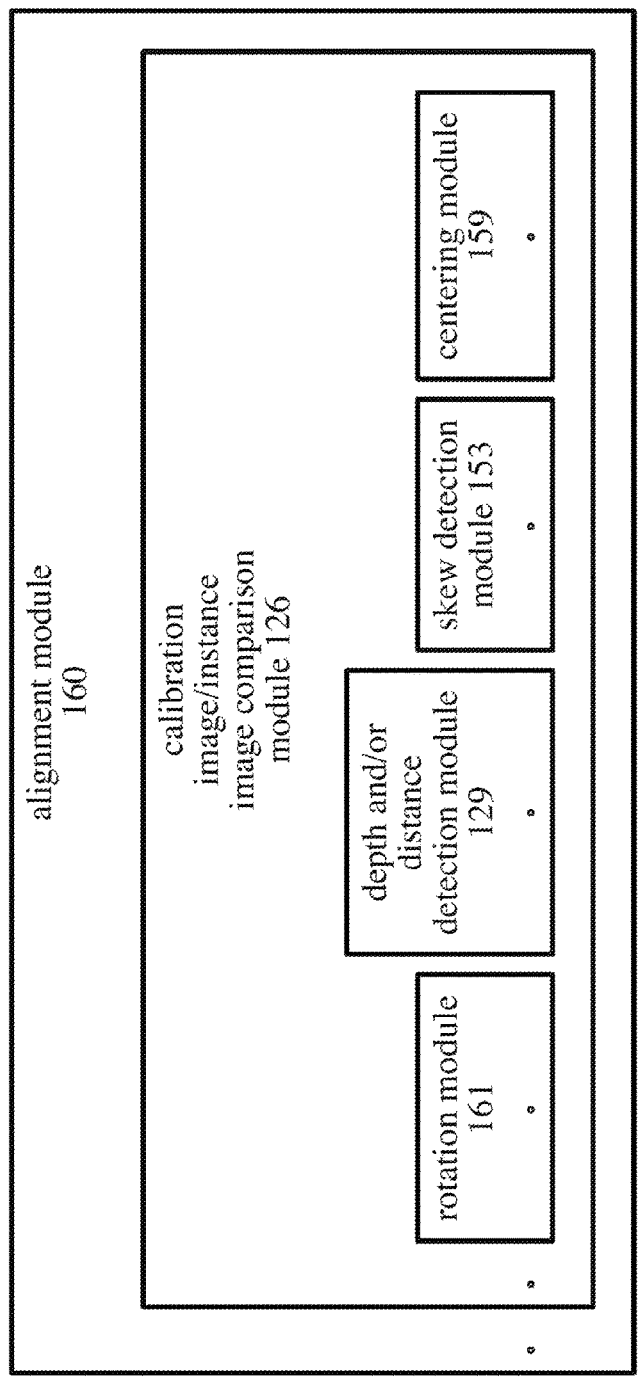
FIG. 19 is a diagram view which shows the alignment module and its sub modules.

Referring now to FIG. 19, the calibration image/instance image comparison module 126 comprises a module that coordinates other modules to compare the calibration image to the instance image in order to determine whether they are aligned within a predetermined tolerance. In some embodiments, this module comprises the designation of certain alignment pixels' regions within the calibration image, wherein the presence of overlap of these pixels with the alignment image generates a data property that may be used to effect determination of alignment. The calibration image/instance image comparison module 126 preferably comprises a centering module 159, a skew detection module 153, a depth and/or distance detection module 129, and finally a rotation module 161.

The centering module 159 comprises a module that determines whether the position of the pixels from the instance image indicate that alignment radiation beams are off center relative to the calibration image or within a predetermined tolerance. In some embodiments, this may be one of the parameters that would cause disengagement of the interlock, as a signal that the instance image may be accurately positioned. The skew detection module 153 comprises a module that determines whether the position of the pixels from the instance image indicate that alignment radiation beams are skewed relative to the calibration image or within a predetermined tolerance.

The rotation module 161 comprises a module that may determine whether the position of the pixels from the instance image indicate that alignment radiation beams are at acceptable rotation within a predetermined tolerance. The depth and/or distance detection module 129 comprises a module that may determine whether the position of the pixels from the instance image indicate that alignment radiation beams are at depth or distance within a predetermined tolerance.

Referring now to FIG. 17, the alignment feedback system 142 comprises one or more methods used by the operator to iteratively determine the position of the detector relative to the source in order to get a radiation image from the patient. The alignment feedback system 142 functions to both: (1) communicate with one or more of the calibration image/instance image comparison module, source positioning sensory component 131, detector positioning sensory component 128, alignment information data 140, alignment display system 148 in order to align the detector with the source and to, (2) provide the data for the operator to align the detector or source. The alignment feedback system 142 has an alternative embodiment herein termed the "auto-align" embodiment.

The source positioning sensory component 131 comprises one or more sensors alone or in combination used to detect position changes when the portable radiation source 143 is moved. In some embodiments, it is thought that examples of a source positioning sensory component 131 may include: a multi-axis displacement sensor, an ultrasound sensor, or mems. In some embodiments, it is thought that if the source positioning sensory component 131 is absent then one may use the image processing system 151 without a source positioning sensory component 131.

The detector positioning sensory component 128 comprises one or more sensors alone or in combination used to detect position changes when the detector is moved. In some embodiments, it is thought that examples of a detector positioning sensory component 128 may include: a multi-axis displacement sensor, an ultrasound sensor, or mems. In some embodiments, it is thought that if the detector positioning sensory component 128 is absent then one may use the image processing system 151 without a detector positioning sensory component 128.

The alignment information data 140 comprises the data that comprises an instance of an alignment beam calibration system 139. Such as an alignment beam calibration image 134, an alignment beam instance image 137 or other data processed by the image processing system 151. One goal of the alignment information data 140 is to give a feedback on the alignment of a radiation source and a detector.

Figure 20:
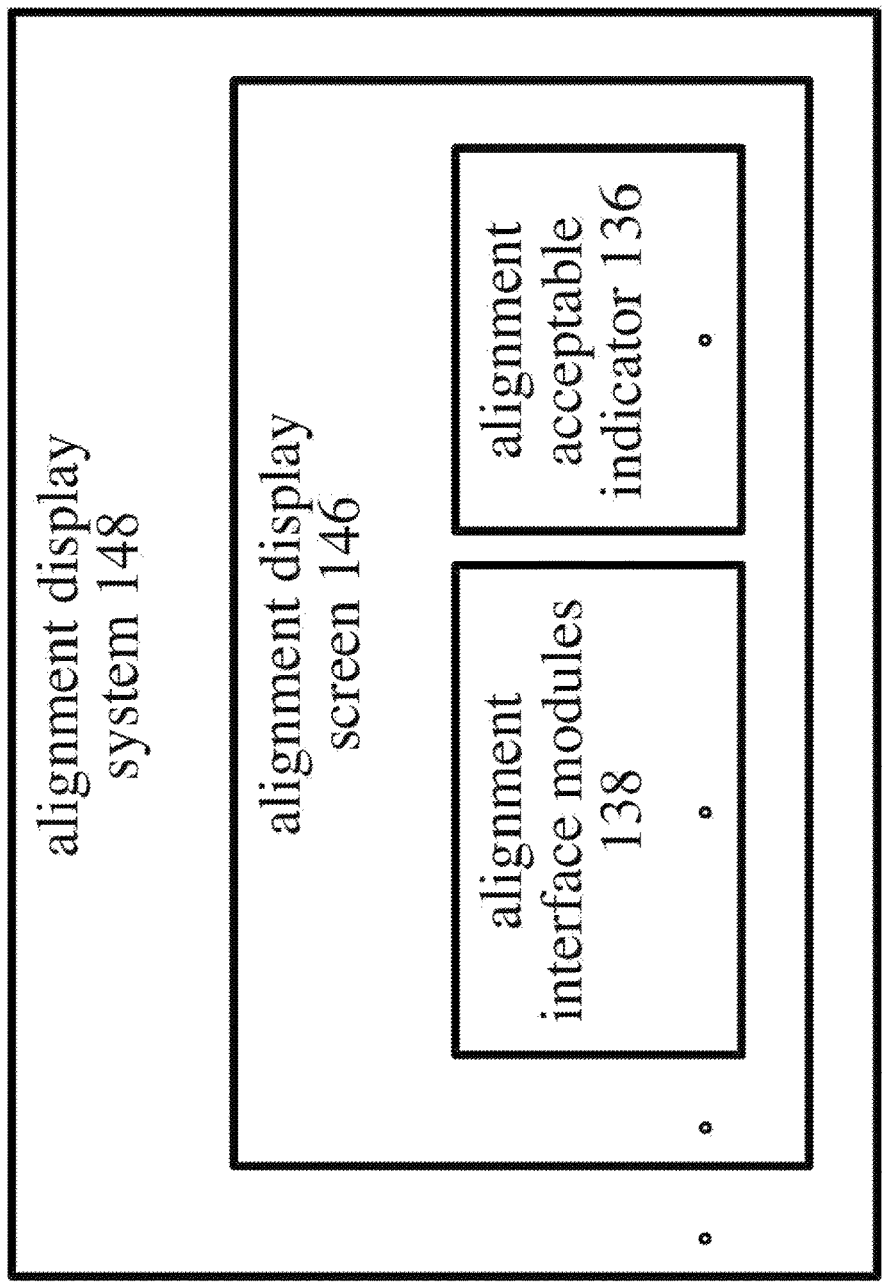
FIG. 20 is a diagram view which shows the alignment display system and its components.

Referring now to at least FIG. 20, the alignment display system 148 comprises hardware and software components that give operator feedback on the positioning of the system so that they may reposition and/or take an x-ray. The alignment display system 148 preferably comprises the alignment display screen 146.

The alignment display screen 146 comprises screen that displays one or more interfaces for determining positioning. In some embodiments, it is thought that examples of an alignment display screen 146 may include: an eidophor, an electroluminescent display, an electronic paper display, an E-ink display, a gyricon, an light emitting diode (LED) display, a cathode ray tube (CRT) display, a liquid-crystal display (LCD), a twisted nematic field effect, an led-back lit display, led, a blue phase mode LCD, IPS panel, a plasma display, plasma display panel, alternate lighting of surfaces display, an organic light-emitting diode (OLED), an amoled display, an organic light-emitting transistor, a surface-conduction electron-emitter display, a field emission display, a laser video display, laser tv, a quantum dot laser, quantum dot, a liquid-crystal laser, liquid crystal, a microelectromechanical systems (MEMS) display, an interferometric modulator display (IMOD), time-multiplexed optical shutter (TMOS), digital micro shutter display (DMS), a quantum dot display, a ferro liquid crystal display, ferro liquid crystal display, a thick-film dielectric electroluminescent technology, a telescopic pixel display, or a laser-powered phosphor display. The alignment display screen 146 preferably comprises the alignment acceptable indicator 136 and the alignment interface modules 138.

The alignment interface modules 138 comprises one or more interfaces for displaying positioning information of alignment feedback system 142. The radiation source exposure interlock 132 comprises a programmatic and/or physical means to immediately shutdown and or prevent the initiation of x-rays from the radiation source.

Referring now to FIG. 2, after repositioning, when the detector and source are aligned within the predetermined tolerance (Step 115) then radiographic images of one or more images or video is captured (Step 117). Preferably, if the video images are detected as being misaligned, during imaging, the interlock would be activated until repositioning occurred. In some embodiments, before taking the radiographic images there may be an enactment of determining the radiation dose, prior to imaging, with an APR. (Step 116). This may occur at various places in the procedure prior to calibration, or post calibration.

The APR comprises an interactive system that allows an operator to configure the dose of radiation to be used for capturing an image/video for a patient. The term software comprises a collection of p and related data. The database comprises an organized collection of data with a software system designed to allow the definition, creation, querying, update, and administration of databases.

Figure 8:
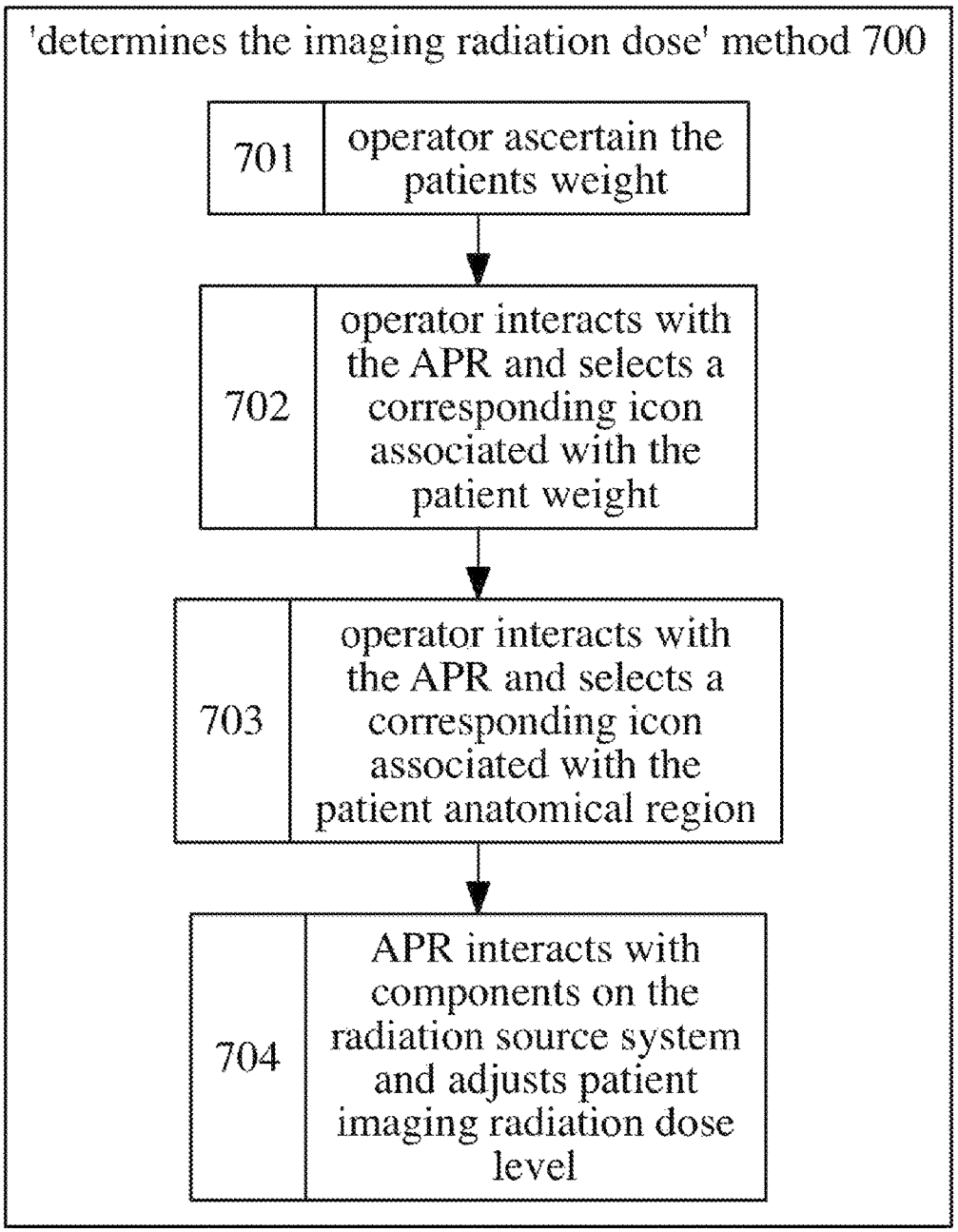
FIG. 8 is a diagram view which shows the method for determining the radiation dose.

An example method for determining the radiation dose may be as follows: Next, referring now to FIG. 8, operator ascertain the patients weight (Step 701). An operator interacts with an APR and selects a corresponding icon associated with the patient weight (Step 702). Next, an operator interacts with the APR and selects a corresponding icon associated with the patient anatomical region (Step 703). Next, an APR interacts with components on the radiation source system 149 and adjusts patient imaging radiation dose level (Step 704).

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the embodiments disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific embodiments, at least some of the features or functionalities of the various embodiments disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some embodiments, at least some of the features or functionalities of the various embodiments disclosed herein may be implemented in one or more virtualized computing environments (e.g., network computing clouds, virtual machines hosted on one or more physical computing machines, or other appropriate virtual environments).

Referring now to FIG. 22, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be adapted to communicate with a plurality of other computing devices, such as clients or servers, over communications networks such as a wide area network a metropolitan area network, a local area network, a wireless network, the Internet, or any other network, using known protocols for such communication, whether wireless or wired.

In one embodiment, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one embodiment, a computing device 10 may be configured or designed to function as a server system utilizing CPU 12, local memory 11 and/or remote memory 16, and interface(s) 15. In at least one embodiment, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some embodiments, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a specific embodiment, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a Qualcomm SNAPDRAGON™ or Samsung EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one embodiment, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™ THUNDERBOLT™, PCI, parallel, radio frequency (RF), BLUETOOTH™, near-field communications (e.g., using near-field magnetics), 802.11 (Wi-Fi), frame relay, TCP/IP, ISDN, fast Ethernet interfaces, Gigabit Ethernet interfaces, Serial ATA (SATA) or external SATA (eSATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 22 illustrates one specific architecture for a computing device 10 for implementing one or more of the inventions described herein, it is by no means the only device architecture on which at least a portion of the features and techniques described herein may be implemented. For example, architectures having one or any number of processors 13 may be used, and such processors 13 may be present in a single device or distributed among any number of devices. In one embodiment, a single processor 13 handles communications as well as routing computations, while in other embodiments a separate dedicated communications processor may be provided. In various embodiments, different types of features or functionalities may be implemented in a system according to the invention that includes a client device (such as a tablet device or smartphone running client software) and server systems (such as a server system described in more detail below).

Regardless of network device configuration, the system of the present invention may employ one or more memories or memory modules (for example, remote memory block 16 and local memory 11) configured to store data, program instructions for the general-purpose network operations, or other information relating to the functionality of the embodiments described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a Java™ compiler and may be executed using a Java virtual machine or equivalent, or files containing higher level code that may be executed by the computer using an interpreter (for example, scripts written in Python, Perl, Ruby, Groovy, or any other scripting language).

Figure 23:
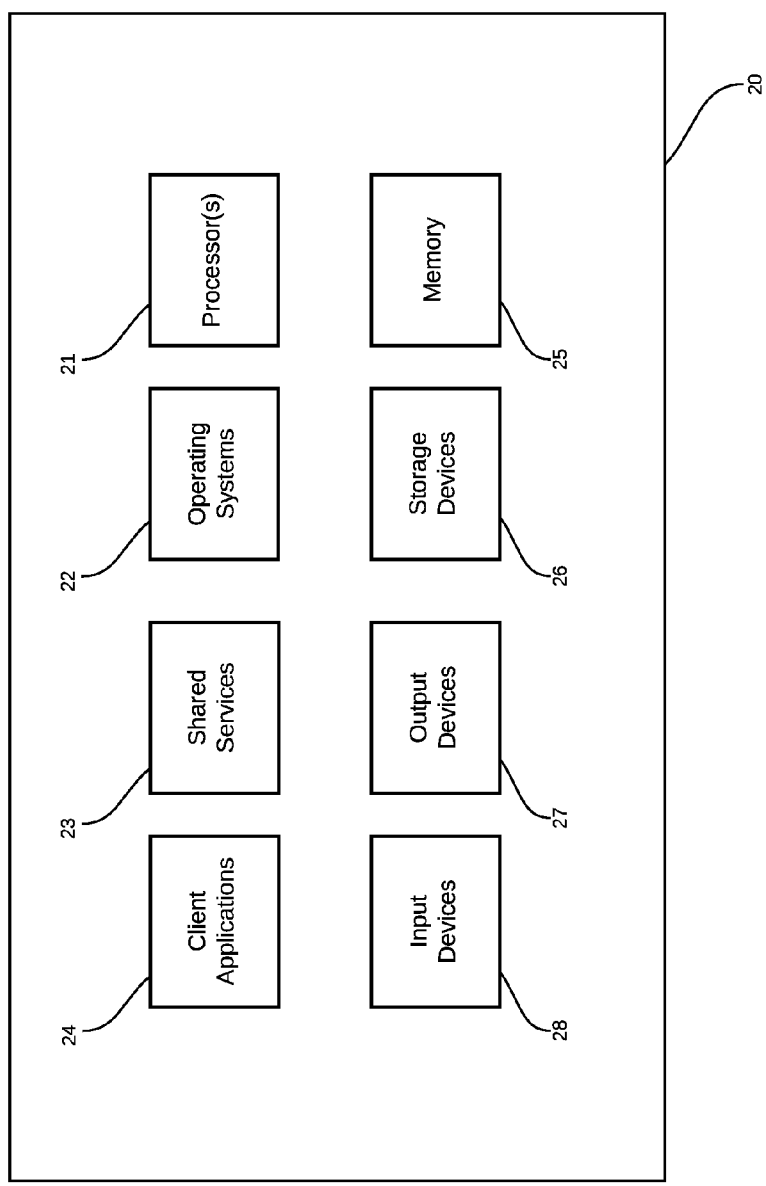
FIG. 23 is a block diagram illustrating an exemplary logical architecture for a client device, according to an embodiment of the invention.

In some embodiments, systems according to the present invention may be implemented on a standalone computing system. Referring now to FIG. 23, there is shown a block diagram depicting a typical exemplary architecture of one or more embodiments or components thereof on a standalone computing system. Computing device 20 includes processors 21 that may run software that carry out one or more functions or applications of embodiments of the invention, such as for example a client application 24. Processors 21 may carry out computing instructions under control of an operating system 22 such as, for example, a version of Microsoft's WINDOWS™ operating system, Apple's Mac OS/X or iOS operating systems, some variety of the Linux operating system, Google's ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 25). Examples of storage devices 26 include flash memory, magnetic hard drive, CD-ROM, and/or the like.

Figure 11:
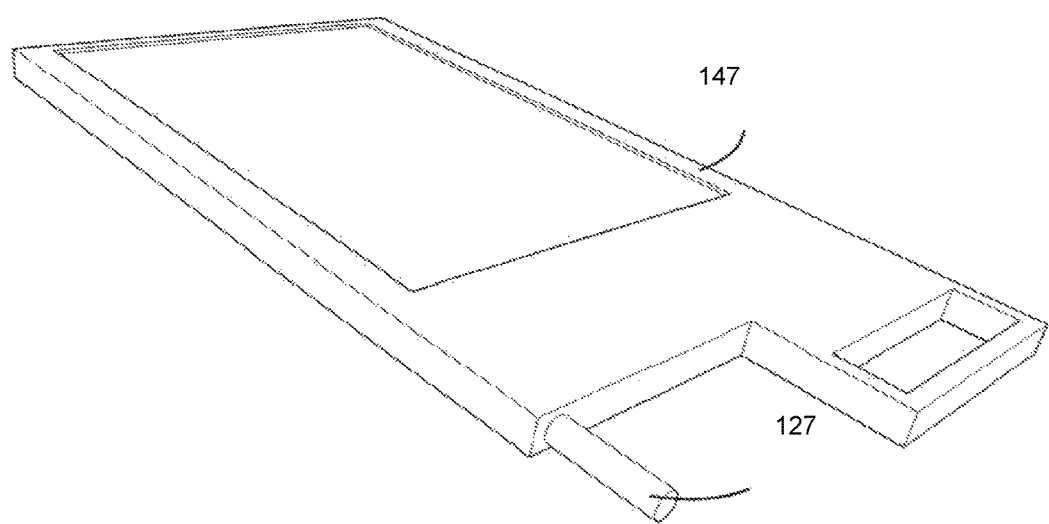
FIG. 11 is a perspective view which shows portable detector.
Figure 12:
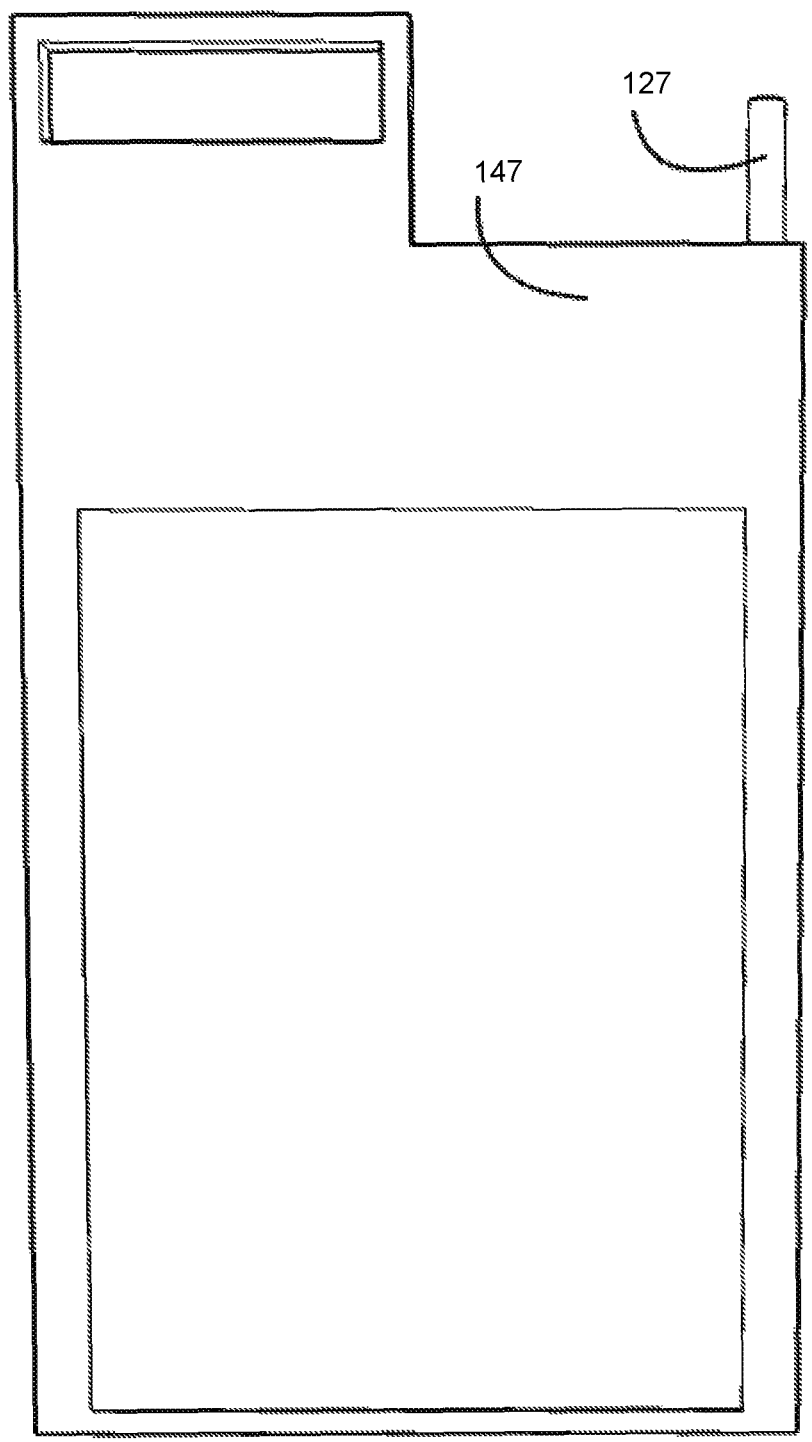
FIG. 12 is a birds-eye view which shows portable detector.
Figure 13:
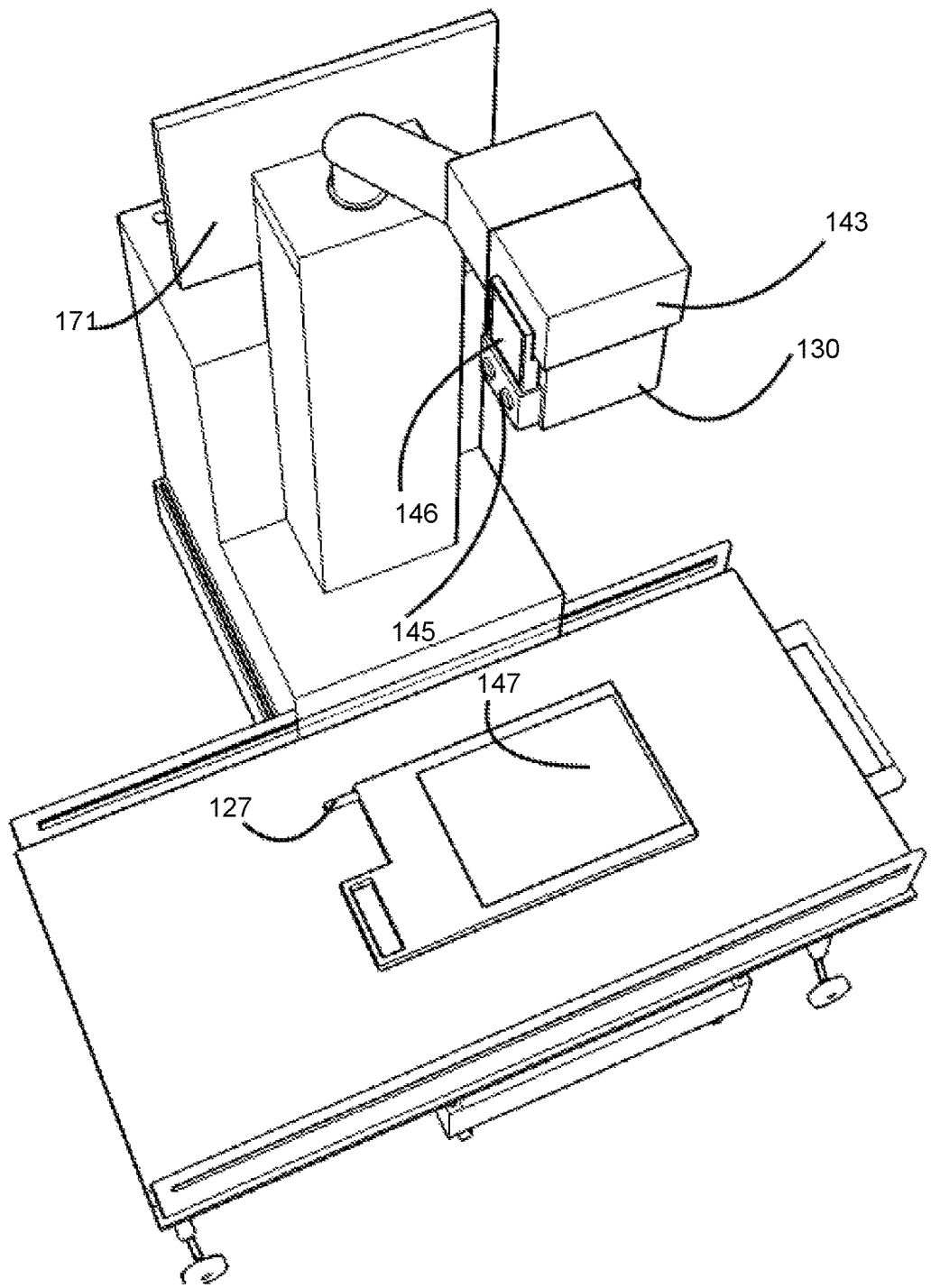
FIG. 13 is a perspective view which shows the radiation source for imaging a patient aligned with a portable detector for calibration.
Figure 14:
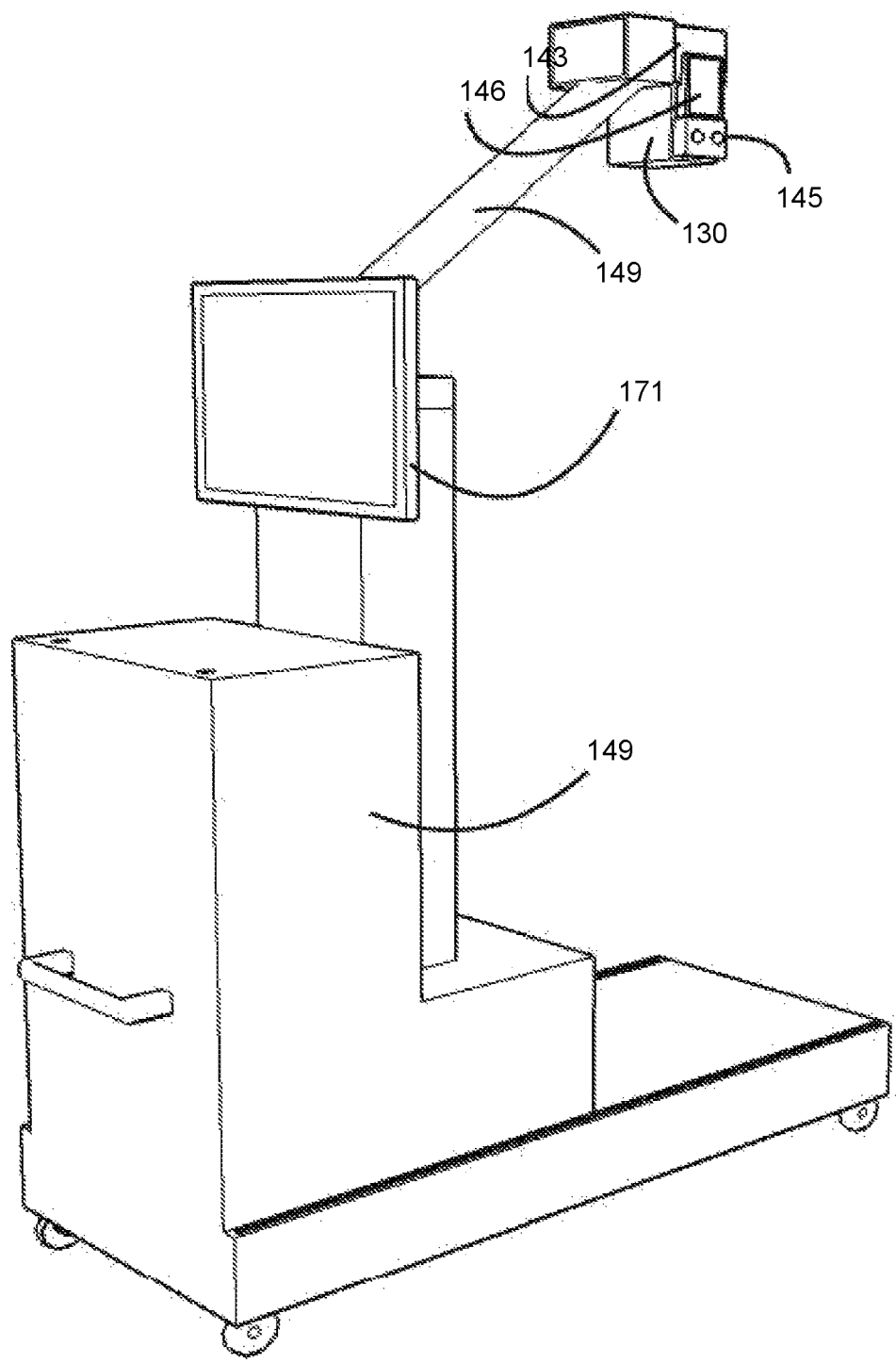
FIG. 14 is a perspective view which shows the radiation source system, alignment display and computer.
Figure 15:
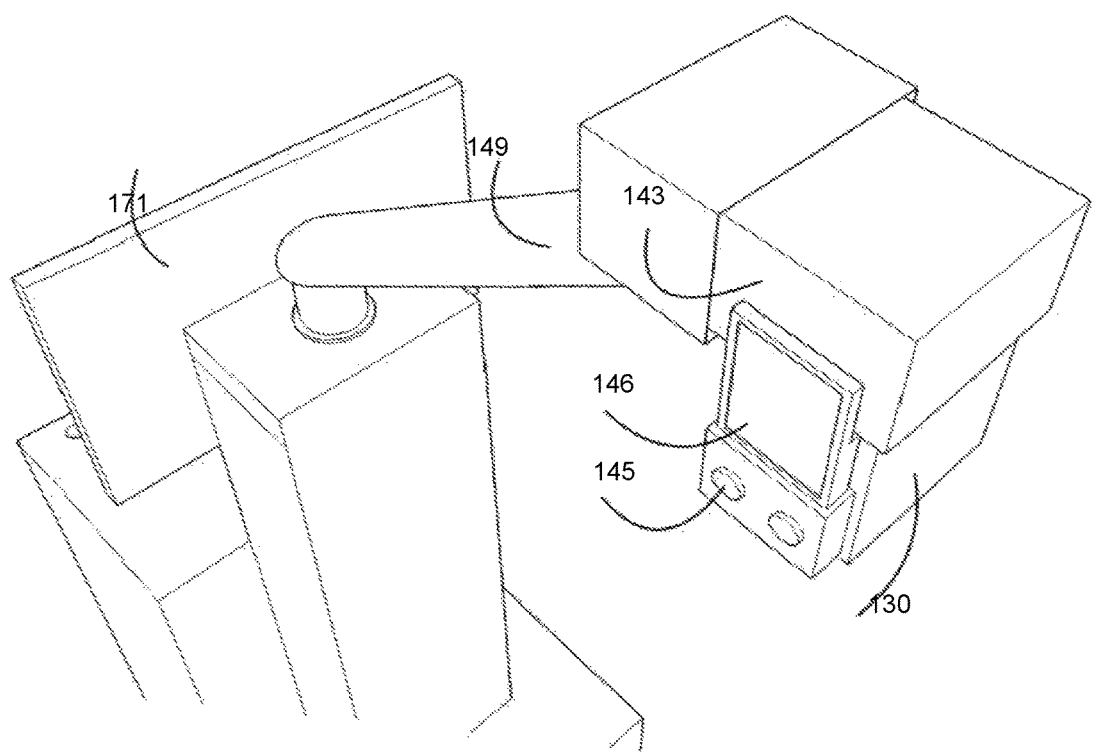
FIG. 15 is a perspective view which shows the radiation source system and alignment display.
Figure 16:
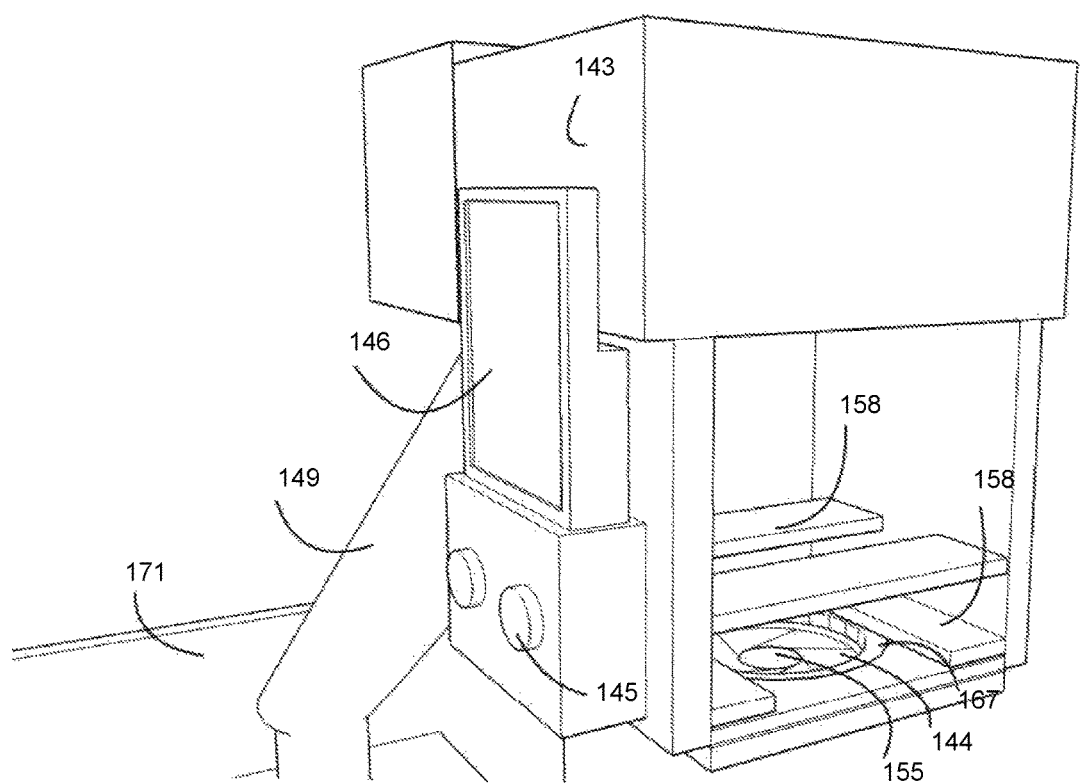
FIG. 16 is a perspective view which shows the alignment beam generating components below the radiation source.
Figure 24:
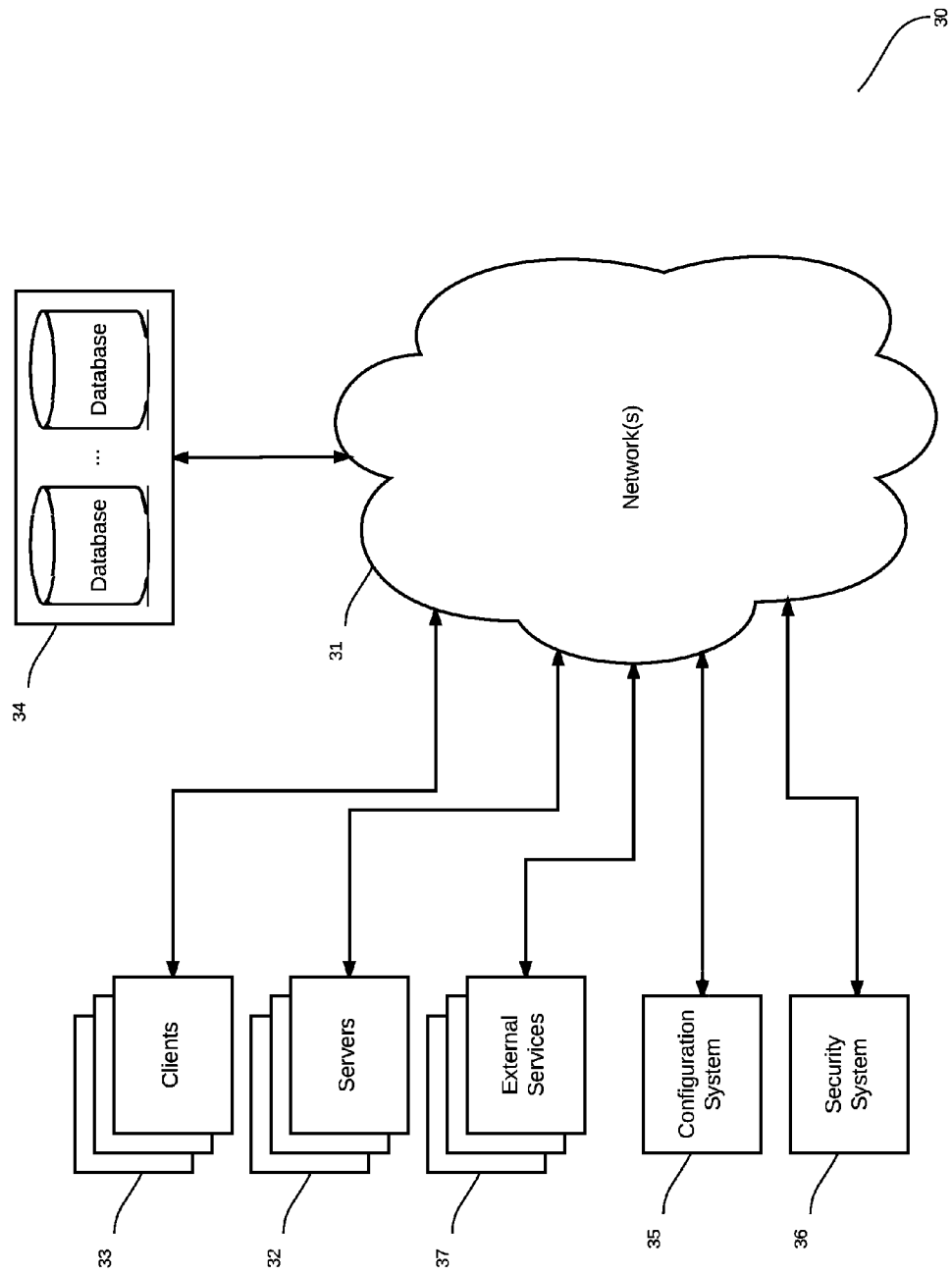
FIG. 24 is a block diagram showing an exemplary architectural arrangement of clients, servers, and external services, according to an embodiment of the invention.

In some embodiments, systems of the present invention may be implemented on a distributed computing network, such as one having any number of clients and/or servers. Referring now to FIG. 24, there is shown a block diagram depicting an exemplary architecture 30 for implementing at least a portion of a system according to an embodiment of the invention on a distributed computing network. According to the embodiment, any number of clients 33 may be provided. Each client 33 may run software for implementing client-side portions of the present invention; clients may comprise a system 20 such as that illustrated in at least FIG. 11. In addition, any number of servers 32 may be provided for handling requests received from one or more clients 33. Clients 33 and servers 32 may communicate with one another via one or more electronic networks 31, which may be in various embodiments any of the Internet, a wide area network, a mobile telephony network (such as CDMA or GSM cellular networks), a wireless network (such as Wi-Fi, WiMAX, LTE, and so forth), or a local area network (or indeed any network topology known in the art; the invention does not prefer any one network topology over any other). Networks 31 may be implemented using any known network protocols, including for example wired and/or wireless protocols.

In addition, in some embodiments, servers 32 may call external services 37 when needed to obtain additional information, or to refer to additional data concerning a particular call. Communications with external services 37 may take place, for example, via one or more networks 31. In various embodiments, external services 37 may comprise web-enabled services or functionality related to or installed on the hardware device itself. For example, in an embodiment where client applications 24 are implemented on a smartphone or other electronic device, client applications 24 may obtain information stored in a server system 32 in the cloud or on an external service 37 deployed on one or more of a particular enterprise's or user's premises.

In some embodiments of the invention, clients 33 or servers 32 (or both) may make use of one or more specialized services or appliances that may be deployed locally or remotely across one or more networks 31. For example, one or more databases 34 may be used or referred to by one or more embodiments of the invention. It should be understood by one having ordinary skill in the art that databases 34 may be arranged in a wide variety of architectures and using a wide variety of data access and manipulation means. For example, in various embodiments one or more databases 34 may comprise a relational database system using a structured query language (SQL), while others may comprise an alternative data storage technology such as those referred to in the art as "NoSQL" (for example, Hadoop Cassandra, Google BigTable, and so forth). In some embodiments, variant database architectures such as column-oriented databases, in-memory databases, clustered databases, distributed databases, or even flat file data repositories may be used according to the invention. It will be appreciated by one having ordinary skill in the art that any combination of known or future database technologies may be used as appropriate, unless a specific database technology or a specific arrangement of components is specified for a particular embodiment herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, most embodiments of the invention may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments of the invention without limitation, unless a specific security 36 or configuration system 35 or approach is specifically required by the description of any specific embodiment.

Figure 25:
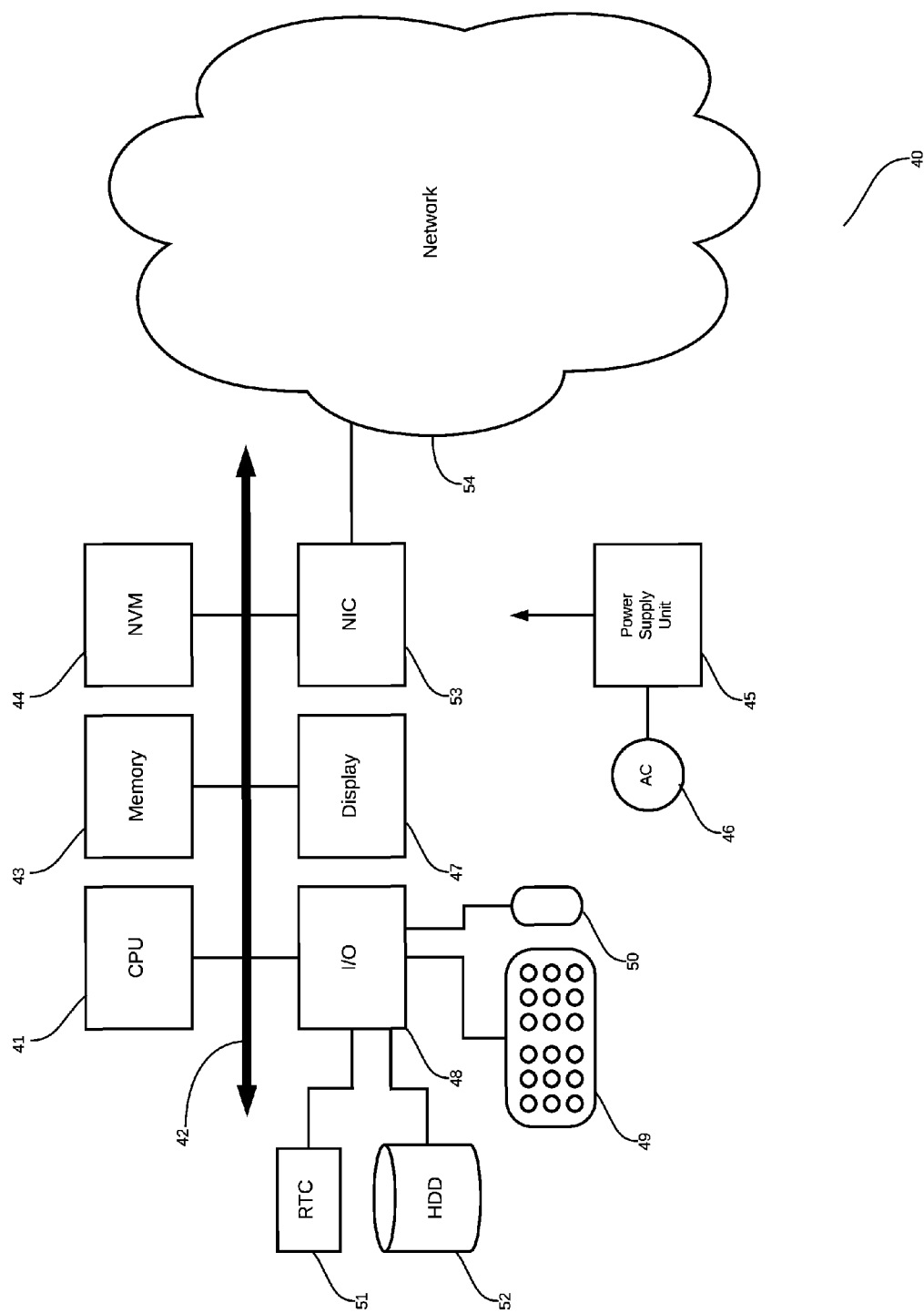
FIG. 25 is another block diagram illustrating an exemplary hardware architecture of a computing device used in various embodiments of the invention.

FIG. 25 shows an exemplary overview of a computer system 40 as may be used in any of the various locations throughout the system. It is exemplary of any computer that may execute code to process data. Various modifications and changes may be made to computer system 40 without departing from the broader spirit and scope of the system and method disclosed herein. CPU 41 is connected to bus 42, to which bus is also connected memory 43, nonvolatile memory 44, display 47, I/O unit 48, and network interface card (NIC) 53. I/O unit 48 may, typically, be connected to keyboard 49, pointing device 50, hard disk 52, and real-time clock 51. NIC 53 connects to network 54, which may be the Internet or a local network, which local network may or may not have connections to the Internet. Also, shown as part of system 40 is power supply unit 45 connected, in this example, to ac supply 46. Not shown are batteries that could be present, and many other devices and modifications that are well known but are not applicable to the specific novel functions of the current system and method disclosed herein. It should be appreciated that some or all components illustrated may be combined, such as in various integrated applications (for example, Qualcomm or Samsung SOC-based devices), or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

Figure 26:
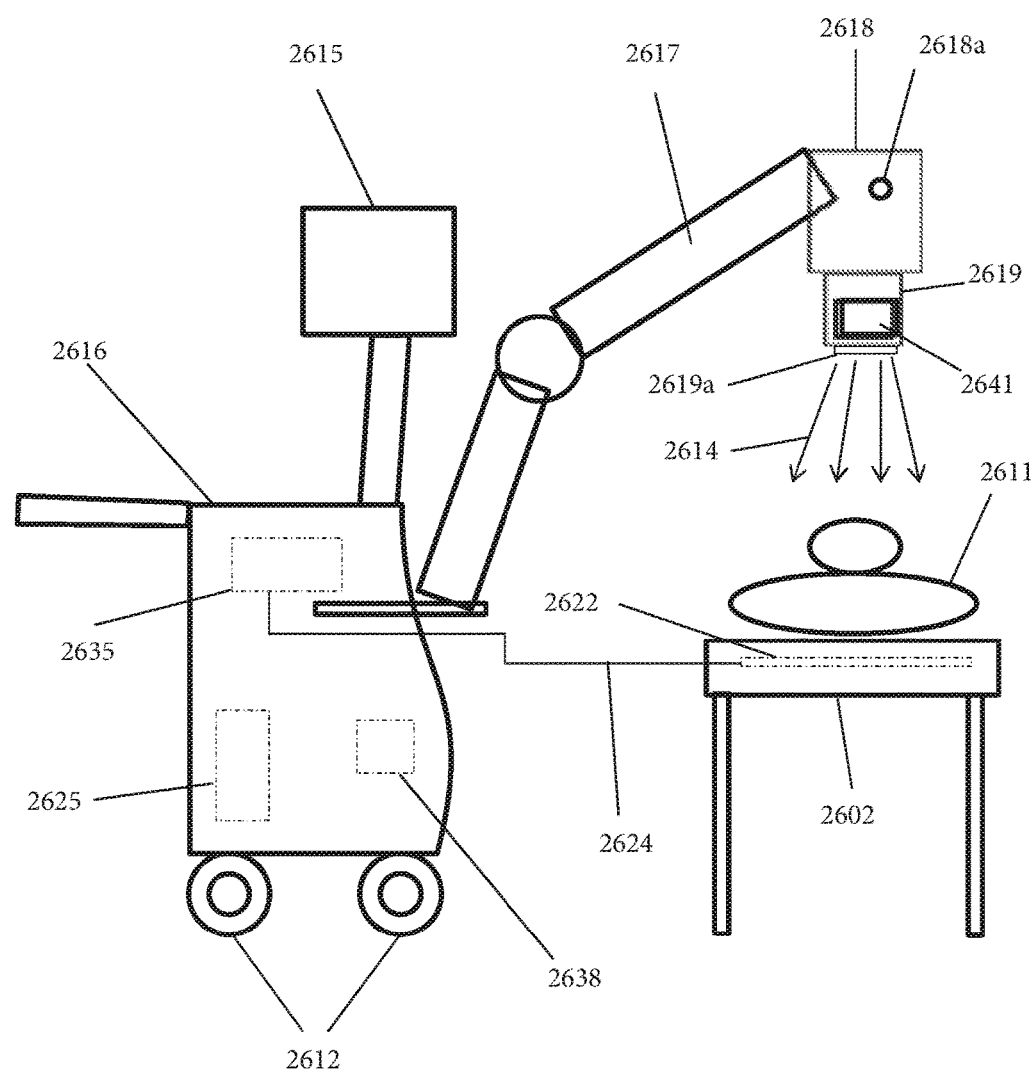
FIG. 26 illustrates a side view of a mobile imaging system applying radiation to a subject in accordance with a preferred embodiment of the invention.

A mobile radiography imaging system, comprising a portable radiation source (such as, e.g., an X-ray source 2618 as seen in FIG. 26) adapted to move in all degrees of freedom; a portable detector (such as a portable detector 2622 as seen in FIG. 26) operable to detect the radiation from the radiation source 2618, wherein the detector 2622 is adapted to move independently of the radiation source in all degrees of freedom. The patient 2611 may not necessarily be in a horizontal position for the X-Ray examination, but may be at an angle, depending on the type of examination required and the ability to move the patient 2611 for the examination. More importantly, if an X-Ray radiograph is captured and the portable detector 2622 and X-Ray source 2618 are not aligned within a predetermined tolerance, the quality and amount of radiation could be comprised, usually causing a retake of the X-Ray radiograph, requiring the patient 2611 to receive additional radiation dose. To perform fluoroscopic procedures, certain governmental agencies, e.g., the US FDA may require that the X-ray source and portable detector must be aligned within a predetermined tolerance. Thus, if the X-ray source 2618 and portable detector 2622 are not aligned within the predetermine tolerance, in accordance with this invention, a radiation source exposure interlock 2618a (as seen, e.g., on FIG. 26) should be activated preventing the X-ray source from producing radiation.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Although a radiographic system is described in this description, the concepts are equally applicable to a fluoroscopic system or a radiographic/fluoroscopic system as well. In fact, this system of this invention is in many respects particularly and preferably adapted for use in fluoroscopic procedures, because of the need for safe control of X-ray emissions from a pulsed or continuance radiation source employed during fluoroscopic procedures. The safety features of this system facilitate the judicious use of and exposure to X-ray radiation during fluoroscopic procedures carried out using a mobile system, and is particular beneficial when applied to subjects who are immobile or fragile and cannot be ported easily for radiological procedures.

Figure 27:
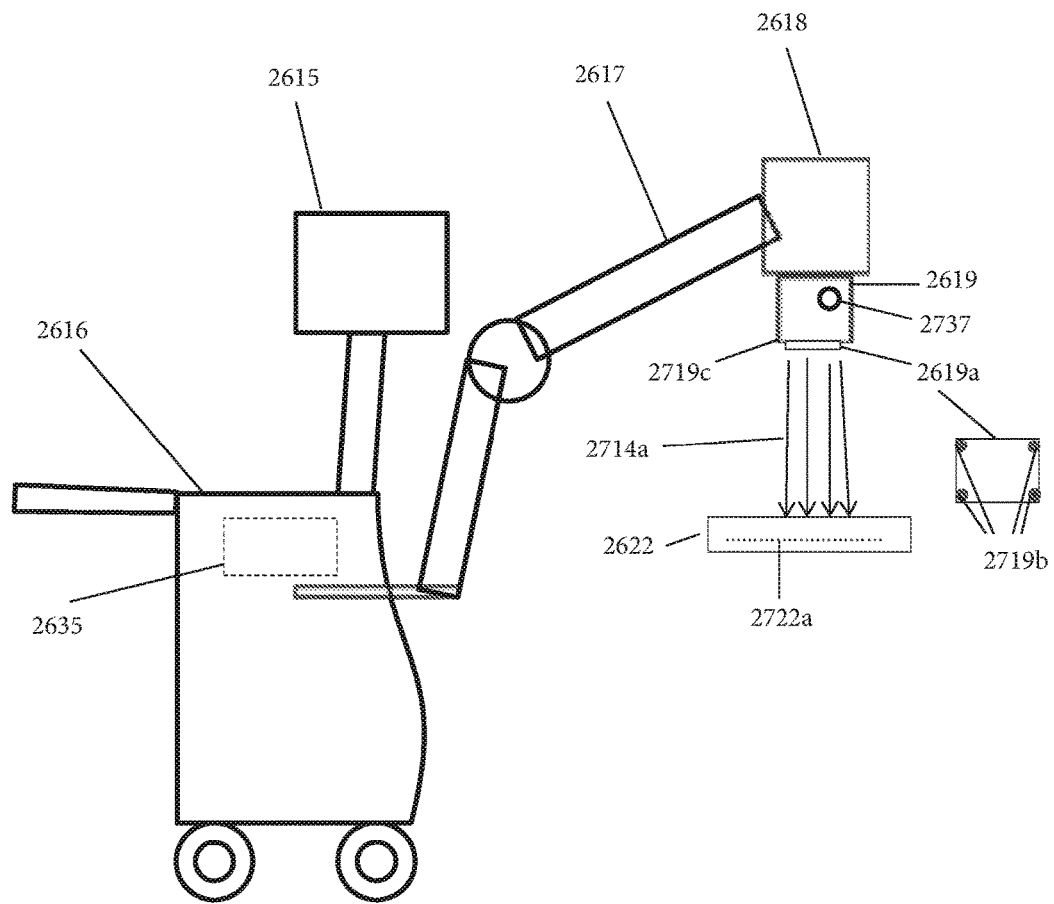
FIG. 27 illustrates more particularly in a side view features of the X-ray source collimator, and positioning plate of the device of FIG. 26.

Referring generally to FIGS. 26 and 27, a mobile X-ray imaging system is presented, referenced generally by reference numeral 2616. In the illustrated embodiment, the mobile X-ray imaging system 2616 is a digital X-ray system that is designed both to acquire radiographic image data and to process the image data for display in accordance with the present techniques. In particular, the system 2616 is operable to produce both radiographic images and fluoroscopic images.

In a preferred embodiment, the mobile radiology imaging system 2616 generally comprises a portable cart having caster wheels 2612, a radiation (X-ray) source 2618 operatively attached to articulating arm 2617 and capable of moving in all degrees of freedom, and a portable flat-panel digital radiation (X-ray) detector 2622. Importantly, the X-ray source 2618 and the detector 2622 are capable of producing both radiographic (via single radiation emissions) and fluoroscopic X-ray images (via pulse or continuance radiation emissions). The imaging system 2616 also includes a collimator 2619 attach to the radiation source 2618, which permits a controlled stream of radiation 2614 to pass into a region in which a patient 2611 is positioned on a table 2602. The collimator also includes positioning plate interlock 2719c, and a positioning plate or lens 2619a with at least one strategically placed positioning aperture 2719b. The positioning plate 2619a can be attached to the collimator. The positioning plate 2619a is preferably positioned between the radiation source and the detector. The positioning plate is configured to block substantially all radiation. The positioning aperture 2719b is sized and configured to allow one or more small alignment radiation beams 2714a to be emitted and pass through the positioning plate to strike the detector 2622. Advantageously, the size of the positioning aperture helps to ensure that a patient receives a low absorbed dose of radiation during the alignment process of the X-ray source to the detector. The size of the positioning aperture may vary, but in certain aspects of the invention will be no greater than about 1 millimeter in diameter, and in other aspects of the invention, the number of positioning apertures is preferably 4. The positioning plate 2619a also insures that the stream of radiation 2614 does not exceed the size of the detector 2622. In an embodiment, the positioning plate 2619a can comprise one or more internal collimator shutter blades. For example, the positioning aperture 2719b can be formed in the internal collimator shutter blades or the internal collimator shutter blades can be adjusted to form a positioning aperture 2719b which will only allow a small positioning radiation beam 2714a to be emitted through the internal collimator shutter blades. The collimator 2619 can be a computer control programmable collimator that will not allow the controlled stream of radiation 2614 to exceed the size of the detector 2622. The controlled stream of radiation 2614 passes through the patient 2611 and impacts the detector 2622. The detector 2622 converts the X-ray photons received on its surface to lower energy photons, and subsequently to electric signals, which are acquired and processed to reconstruct an image of the features within the patient 2611. As can be appreciated from FIG. 26, alignment between the radiation source 2618 and the detector 2622 and size of stream of radiation 2614 is of critical importance. If the radiation source 2618 and the detector 2622 are not aligned, a portion of the stream of radiation 2614 may not passes through the patient 2611 at the intended position, orientation or angle, so the stream of radiation 2614 cannot be properly received by the detector 2622, and an accurate image of the patient 2611 cannot be obtained. Furthermore, even if the detector 2622 is directly in line with the radiation source 2618, the detector 2622 must be oriented such that its plane is perpendicular to the radiation source 2618 for proper detection of the radiation 2614. In addition, for fluoroscopic, alignment the stream of radiation 2614 must conform to FDA or certain government standards which requires alignment of the radiation stream size of X-ray source 2618 to detector 2622, if X-ray source 2618 is not within alignment tolerance, or stream of radiation 2614 is not the proper size, the alignment system must inhibit X-ray source 2618 from producing radiation 2614.

In an operating configuration, a patient 2611 is positioned on a table or other patient support 27 and located between the radiation source 2618 and the detector 2622. The detector 2622 can be coupled via data cable 2624 to a workstation computer 2635 which commands acquisition of the signals generated in the detector 2622, although wireless communication between the detector 2622 and the computer is the more preferred method. As the detector receives radiation 2614 that passes through the patient 2611, imaging data is transmitted to the workstation computer 2635. In most cases, the workstation computer 2635 may also execute various signal processing and filtration functions, such as for initial adjustment of dynamic ranges, interleaving of digital image data, and so forth. The workstation 2635 also enables a user to control the operation of the system to produce a desired image. Images processed by the workstation 2635 are displayed on a monitor 2615. Electrical power for the radiation source 2618, workstation computer 2635, and the digital detector 2622 is provided by a conventional power supply 2625 located within the cart, and which may be provide by batteries or electrically connected to any available 110 VAC power source.

Because movement of the detector 2622 is independent of the radiation source 2618, it is possible for the stream of radiation 2614 to strike the detector 2622 at an angle or not centered to the detector 2622, producing inaccurate images of the patient 2611. As shown more clearly in FIG. 27, the radiation source collimator 2619 can be provided with a positioning plate 2619a having at least one positioning aperture 2719b that allow only one or more small positioning radiation beams 2714a to be emitted. The detector 2622 contains millions of roughly 0.2 mm pixels 2722a each containing a thin-film transistor form a grid patterned in amorphous silicon on a glass substrate. Each pixel also contains a photodiode which generates an electrical signal in proportion to the light produced by the portion of scintillator layer in front of the pixel. The signals from the photodiodes are amplified and encoded by additional electronics positioned at the edges or behind the sensor array in order to produce an accurate and sensitive digital representation of the radiation beam 2614 or 2714a striking the pixel 2722a.

The detectors 2622 pixel grid pattern provide an accurate location of each pixel 2722a within the detector 2622, the computer 2635 contains software capable of tagging the pixels 2722a as alignment pixels selected to receive the small alignment radiation beams 2714a from the positioning plate 2619a to determine if the X-ray source is aligned to the detector, if the positioning aperture 2719b is not aligned with the tag pixels, the small alignment radiation beams 2714a will strike and activate pixels 2722a other than the tag pixels, the computer 2635 software can calculate the location and orientation (x,y,z, rotation, and tilt) of the activated pixels and then calculate the direction and distance (x.y,z, rotation, and tilt) the X-ray source 2618 or detector 2622 must be moved to attain alignment of the X-ray source to the detector. The radiation source 2618 is repositioned and a second exposure is initiated, the computer 2635 software can calculate the location and orientation (x,y,z, rotation,& tilt) of the activated pixels and then calculate the direction and distance (x.y,z, rotation,& tilt) the X-ray source 2618 or detector 2622 must be moved to attain alignment of the X-ray source to the detector. The radiation source 2618 is repositioned and a second exposure is initiated, the computer 2635 calculates the reposition location of the radiation source 2618 with respect to the detector 2622. If the radiation source 2618 is not aligned to the detector 2622, then the radiation source 2618 or detector 2622 is repositioned and a third exposure is initiated, the operator will perform this process until the icons 3241a-g on the visual display 2641 are aligned.

If the radiation source 2618 and detector 2622 are capable of providing pulse of continuance fluoroscopy, the operator can observe the icons 3241a-g on the visual display 2641 and align the radiation source 2618 to the detector 2622 by observing the icon 3241a-g on the visual display 2641 as the radiation source 2618 or detector 2622 are repositioned, the computer will update the new position of the radiation source 2618 or detector 2622 icon 3241a-g displayed on the visual display 2641 in real time as the radiation source 2618 or detector 2622 is repositioned. The operator would continue repositioning the radiation source 2618 or detector 2622 while observing the icons 3241a-g of the visual display 2641 until the icons 3241a-g are aligned. One can easily align the radiation source 2618 to the detector 2622 by moving the radiation source 2618 or detector 2622 until the icon 3241a-g displayed on the LCD monitor 2641 representing the radiation source 2618 and detector 2622 are aligned to each other.

The system could include a radiation source multi axis motion sensor 18b. A positioning radiation exposure 2714a is initiated, the radiation source collimator positioning plate 2619a and detector pixel grid pattern provide data of which pixel 3022b was strike by the positioning radiation beams 2714a, the data is transmitted to the computer 2635, the computer 2635 process the received data and calculate the present position and orientation of the radiation source 2618 relative to the detector 2622. If the present position of the radiation source 2618 with respect to the detector 2622 is not aligned to within the predetermine tolerance, the radiation source 2618 or detector 2622 must be reposition. The computer 2635 is also in communication with the radiation source multi axis motion sensor 18b, the computer 2635 communicates to the sensor 18b the calculated position and orientation of the radiation source 2618 with respect to the detector 2622 Any movement of the radiation source 2618 is sensed by the sensor 18b, the sensor 18b transmit in real time the movement data of the direction and axis to the computer 2635, the received data is process by the computer 2635 and in real time the computer 2635 updates the location of the radiation source icon on the visual display 2641. One can easily align the radiation source 2618 to the detector 2622 by moving the radiation source 2618 until the icon displayed on the visual display 2641 representing the radiation source 2618 and detector 2622 are aligned to each other. Advantageously, fewer radiation exposure are required, the radiation source multi axis motion sensor 18b provide positioning data to align the radiation source 2618 to the detector 2622 after the initial positioning radiation exposure 2614.

Once alignment has been achieved, the positioning plate 2619a is removed from the path of the radiation beam 2614. The computer 2635 also tags pixels surrounding the outer perimeter of the detector 2622, the outer perimeter pixels are tagged to insure alignment and or maximum radiation beam 2614 size of the X-ray source 2618 to the detector 2622 is maintain. If the tagged outer perimeter pixels receive radiation, this condition would indicate that the X-ray source 2618 is no longer aligned or the radiation beam 2614 has exceed the size of the detector 2622, the computer 2635 will immediately activate the X-ray source radiation interlock 2618a to terminate radiation output. The computer 2635 establishes both the location and orientation of the respective radiation source 2618 and detector 2622 relative to one another. The computer 2635 provides data to align the detector 2622 with the radiation source 2618 to ensure that the radiation 2614 from the radiation source 2618 strikes the detector 2622 at the correct angle, position and orientation.

As further illustrated in FIG. 27, the one or more small alignment radiation beams 2714a provided by the positioning plate 2619a strikes and activates respective detector 2622 pixels 2722a, the detector 2622 transmit position signals from the activated pixels to the computer 2635. Those signals are processed by the alignment system software located within computer 2635 to ascertain the orientation, distance, and location of the detector 2622 relative to the radiation source 2618 is aligned normal to the path of stream of radiation 2614 being emitted from the radiation source 2618. The alignment system software within computer 2635 sends process data to visual display 2641, and data received by visual display 2641 visually displays the location and orientation of detector 2622 and the radiation source 2618. When alignment in accordance with predetermined conditions is achieved, the computer 2635 sends an activation signal to the radiation source 2618, whereupon an audible indicator 2737 and/or visual indicator 2641 will activate to notify the operator that radiation 2614 may be administered. The alignment system software may also be operable to indicate when the detector 2622 is within range of the radiation source 2618. Finally, the system 2616 may be connected to the Internet or other communication network so that the images produced by the system 2616 may be sent to a remote user, such as a radiologist's workstation. Importantly, the computer 2635 may also be used to control the radiation source 2618, such that emission of radiation 2614 is prohibited until and unless the proper alignment conditions are achieved. Similarly, the computer 2635 and the alignment software may be programmed to automatically permit emission of a radiation 2614 for either radiographic or fluoroscopy images immediately upon achieving the predetermined alignment conditions. Thus, the present invention may be used to limit patient's 2611 exposure to unnecessary or excessive radiation 2614 in a particular situation due to improper alignment. Until development of this system, such control over the emission of radiation by establishing this "interlock" 2618a between alignment conditions and the radiation source has not been available in portable radiology imaging systems, and particularly in the context of ICU and NICU applications.

Figure 28:
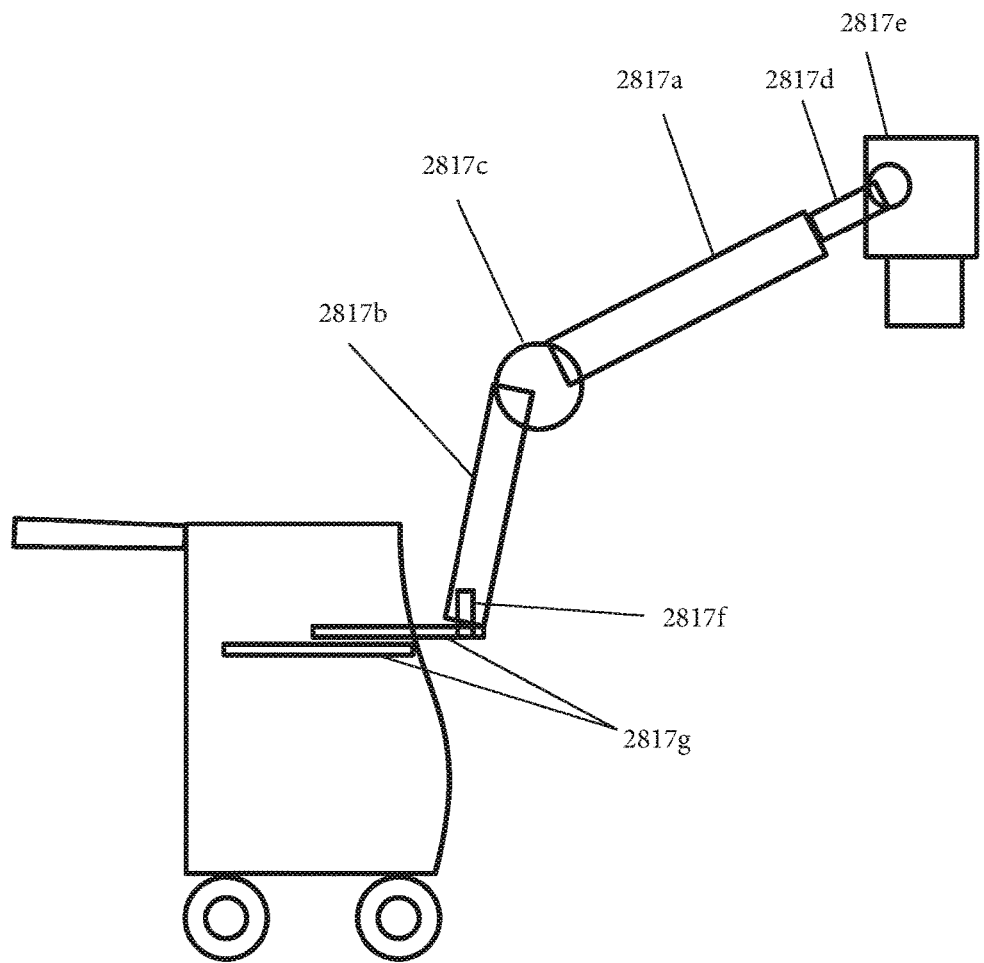
FIG. 28 illustrates the articulating arm of the device of FIG. 26, to provide for X-ray source positioning.

FIG. 28 illustrates the articulating tube support arm 2617 consist of vertical travel arm 2817a, which consist of a, fix vertical support arm 2817b, tube support arm pivot assembly 2817c, tube support arm rotation assembly 2817f, tube support arm longitudinal bearing assembly 2817g, & 2917h. Vertical travel arm 2817a provide support and vertical movement of X-Ray tube assembly 2618, gas springs 17aa & 17bb has a combine pull force to produce a counterbalancing force so X-ray tube assembly 2618 and X-ray collimator 2619 will remain in the vertical position they are place throughout the movement range allowed by pivot assembly 2817c. Fix vertical arm 2817b support the pivot assembly 2817c for vertical travel arm 2817a. Rotation shaft 2817e provides transversal movement of X-Ray tube assembly Longitudinal bearing track assembly 2817g provides longitudinal movement for the X-ray tube assembly 2618. Yoke 3019d provides X-ray tube assembly 2618 to rotate around the axis of vertical travel arm 2817a. Tube rotation assembly 2817e provides X-ray tube assemble to rotate longitudinal about is axis.

Figure 29:
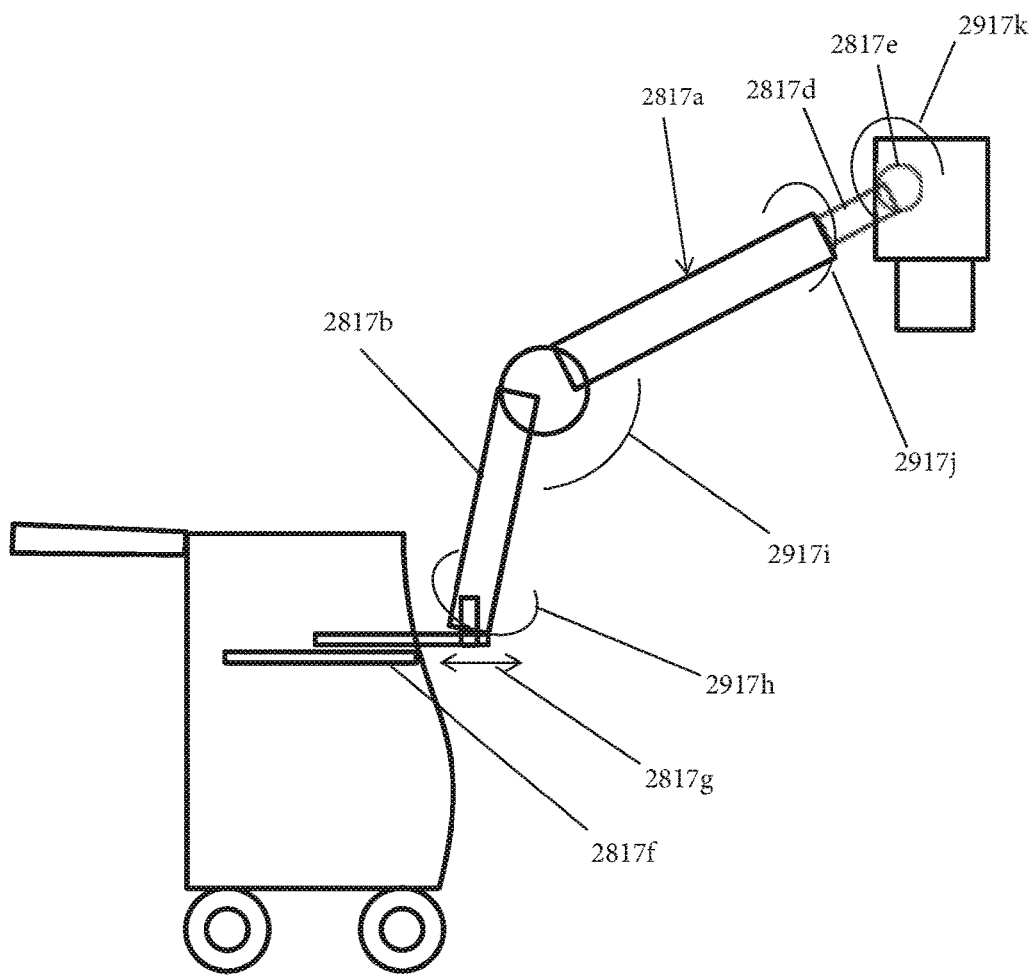
FIG. 29 illustrates range of movement of the articulating arm of the device of FIG. 26, to provide for X-ray source positioning.

FIG. 29 shows range of movement the articulating arm 2617 provides for X-ray source positioning in the device of FIG. 26.

Figure 30A:
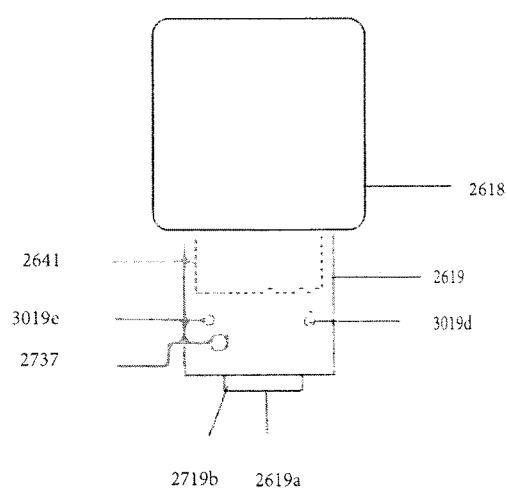
FIGS. 30A & 30B illustrates an enlarged, side, partially phantom view of the portable radiation source and portable X-ray detector of the device if FIG. 26.

FIG. 30a illustrates the portable X-ray source 2618 of the device FIG. 26, comprising X-Ray tube head 2618, X-Ray beam collimator 2619, visual display 2641, collimator light 3019e Laser positioning cross hair 3019d audile indication 2737, and positioning plate 2619a, positioning plate interlock 2719c, Positioning plate 2619a can be housed or fix mounted within the X-Ray beam collimator enclosure 2619.

Figure 30B:
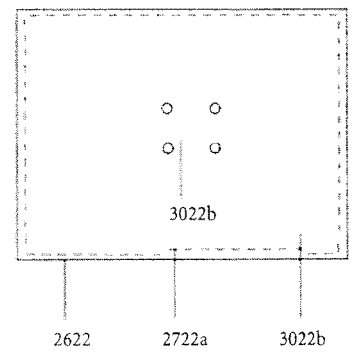

FIG. 30b illustrates the portable detector 2622 of the device, comprising the active imaging area 2722a, and positioning tag pixels area 3022b.

Figure 31:
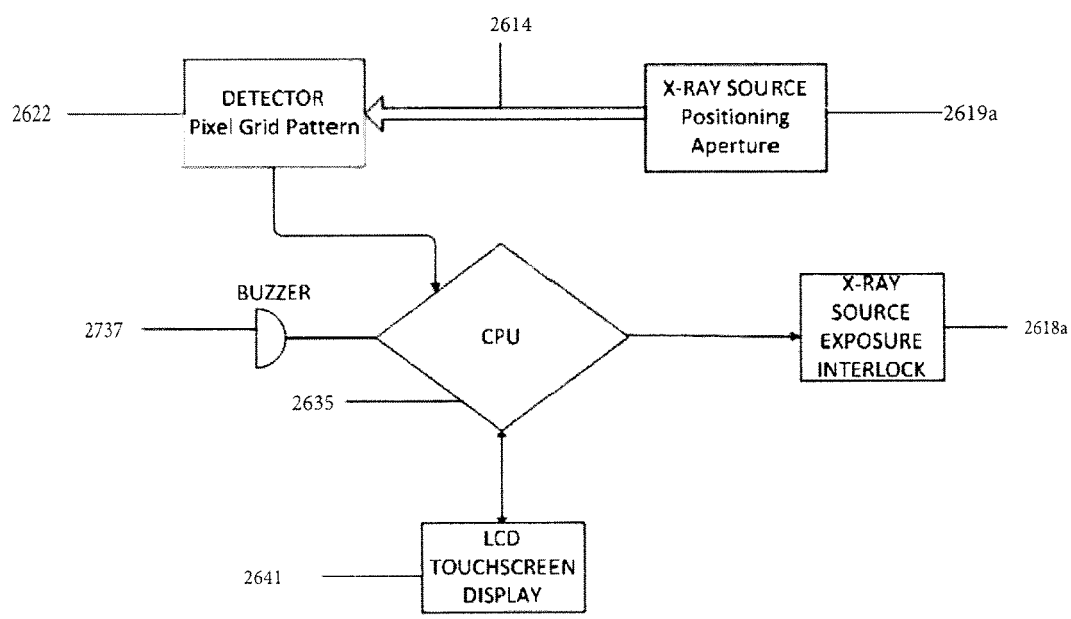
FIG. 31 is a schematic diagram of the computer and certain inputs and outputs present in the device of FIG. 26.

FIG. 31 is a schematic diagram of the FIG. 26 radiation source 2618 collimator 2619 positioning plate 2619a, detector 2622; computer 2635, audible buzzer 2737, radiation source exposure interlock 2618a, and visual display 2641.

Figure 32:
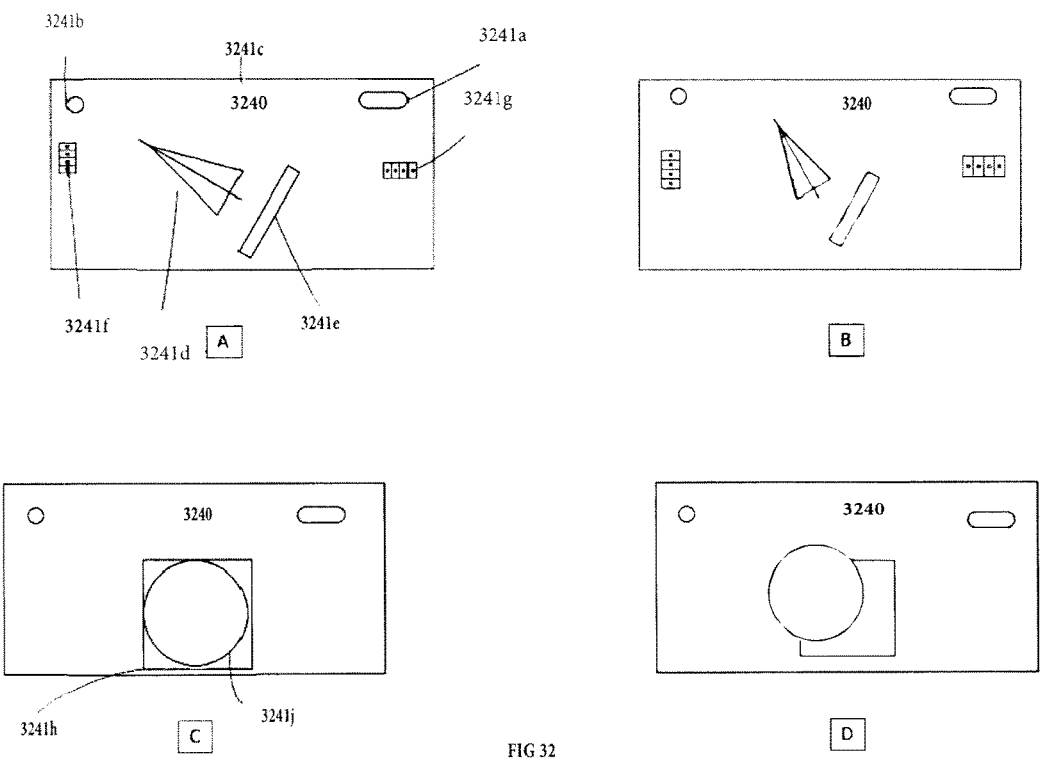
FIG. 32A-32D depicts example representations of different views of the visual display in the embodiment of FIG. 26.
Figure 33:
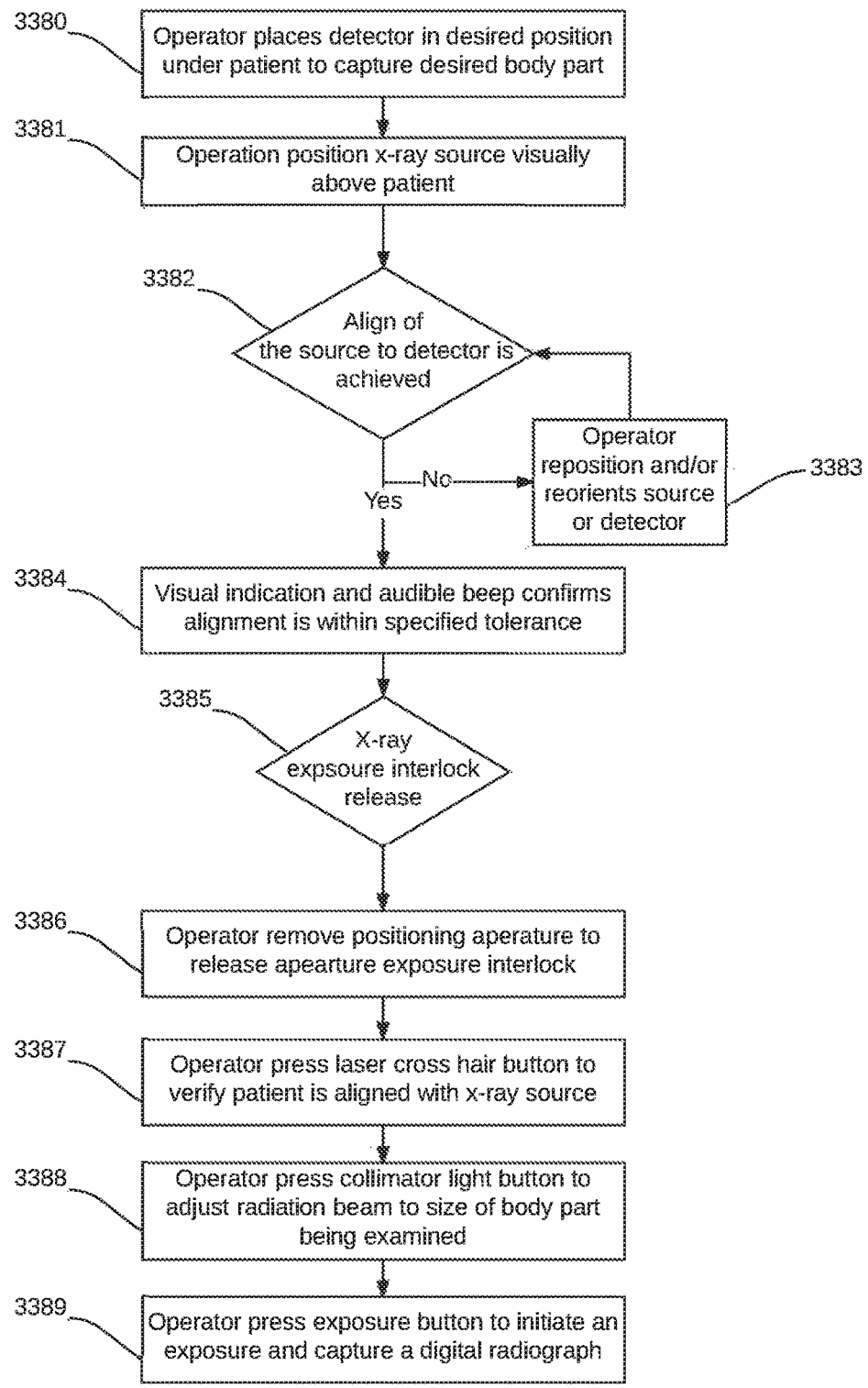
FIG. 33 is a work flow diagram for a typical X-ray examination employing the device of FIG. 26.

FIG. 32 illustrates four (4) alternative examples of the visual display 2641 display of information to assist the operator with alignment of X-Ray source 2618 to the portable detector 2622. These screenshots illustrate examples of the type of information that may be available to the operator for positioning of radiation source 2618 to the portable detector 2622, or portable detector 2622 to the radiation source 2618. Various icons, LEDs, bar graph, or graphic symbols can be used to display position or orientation of radiation source 2618 and detector 2622 on visual display 2641. FIG. 7A shows visual display positioning data if detector is placed at an oblique angle 3241a "Start Icon" initiates calibration and calculation of present position of detector 2622 and radiation source 2618. 3241c displays distance between detector and radiation source, 3241d is radiation source icon, 3241e is detector icon, 3241f is LED bar graph to show longitudinal position, 3241g is LED bar graph to show transverse position, FIG. 7C shows visual display positioning data if detector is place perpendicular: 3241h is the detector, 3241j is the radiation source FIGS. 7B & 7D shows visual display positioning data when detector and radiation source are not aligned. FIG. 33 shows the work flow for a typical X-Ray examination, 3380 the operator first places the portable detector 2622 under the patient (note: the portable detector 2622 is usually no longer visible to the operator after placement) the portable detector 2622 is positioned to insure the body part to be examined is within the active imaging area 2722a of the portable detector. 3381 the operator then positions the portable radiation source 2618 with the aid of the Laser positioning cross hairs 3019*d* The operator positions the positioning plate, selects the "START" icon 3241*a* on visual display to begin position calculation of radiation source 2618 with respect to the detector 2622. System will accurately display location of X-ray source 2618 to the detector 2622, if the X-ray source is aligned within the predetermine tolerance to the detector the icons on the visual display 2641 will illuminate green and an audible signal can sound indicating the X-ray source is aligned to the detector. If the X-ray source is not aligned to the detector the icons will illuminate red indicating the X-ray source is not aligned to the detector, system also provides data of direction, angle, orientation, and distance operator has to move the radiation source and/or detector to align the radiation source and detector within the predetermine tolerances. 3384 Upon successful alignment of radiation source to detector system will active a visual 3241*b* and/or audible signal 44 confirming alignment is within the predetermine tolerance. 3385 System will then release "Radiation interlock" 2618*a*, 3386 operator press laser cross hair button 2719*b* to verify patient is align with radiation source 2618, if patient is not aligned operator moves patient for proper alignment, 3387 operator press collimator light button to active collimator light source which represent size of stream of radiation 2614, operator adjusted light size for size for body part being examined. When all conditions are met, operators can initiate an X-ray exposure and capture the digital radiograph.

FIG. 33 shows the work flow for a typical X-Ray examination employing a device in accordance with a preferred embodiment of the invention. In initial step 3380 the operator first places the detector 2622 under the patient. (Note: the portable detector 2622 is usually no longer visible to the operator after placement.) The detector 2622 is positioned to insure the body part to be examined is within the active imaging area 2722*a* of the portable detector 2622. In step 3381 the operator positions the positioning plate 2619*a* and then position the radiation source 2618 above patient Then select "Start" on visual display 2641. In steps 3382 and 3383 the system will accurately display on visual display 2641 the location of portable detector 2622 with respect to radiation source 2618, and provide data of direction, angle, orientation, and distance that the operator must move the radiation source and/or portable detector to position the radiation source and detector within predetermine tolerances. Upon successful alignment of radiation source 2618 to detector 2622 the system will active in step 3384 a visual 3241*b* and/or audible signal 2737 confirming alignment is within the predetermine tolerance. System will in step 3385 release "Radiation interlock" 2618*a*, and operator will in step 3386 press laser cross hair button 2719*c* to verify patient is aligned with radiation source 2618. If patient is not aligned, operator moves patient for proper alignment. In step 3387, operator presses collimator light button to activate collimator light source which displays a representation of the size of stream of radiation 2614, operator adjusted light size for size for body part being examined, 3388 When all conditions are met, in step 3389 operator can initiate an X-ray exposure and capture the digital radiograph.

In other embodiments, the invention can comprise:

A mobile imaging system, comprising:

a portable radiation source configured to move in all degrees of freedom and to emit radiation, the portable radiation source comprising:

a collimator;

a positioning plate, the positioning plate configured to produce at least one alignment radiation beam from the radiation;

a multi axis motion sensor, the senor is configured to produce position and location of the radiation source data.

a portable detector configured to move independently of the radiation source in all degrees of freedom to detect the radiation, the portable detector comprising at least one pixel, the pixel configured to be activated by the alignment radiation beam; and wherein the positioning plate is positioned between the portable radiation source and the portable detector.

An alignment computer in communication with the portable radiation source and the portable detector, wherein the alignment computer is configured to determine the position of the portable radiation source relative to the position of the portable detector by calculating the location of an activated detector pixel;

The mobile imaging system of A above, wherein at least one positioning aperture is formed in the positioning plate.

The mobile imaging system of A above, wherein the positioning plate comprises at least one internal collimator shutter blade, and wherein at least one positioning aperture is formed in the collimator shutter blade.

The mobile imaging system of A above, wherein the positioning plate comprises at least one collimator internal shutter blade, and wherein the collimator internal shutter blade is configured to be adjusted to form a positioning aperture is formed.

The mobile system of A above, wherein the radiation source contains a multi axis motion sensor to provide location and position of the radiation source.

A tangible non-transitory computer usable medium having computer-readable program code encoded thereon which, when executed, carries out a method comprising determining a spacial position of a portable radiation source relative to a spacial position of a portable detector by calculating the spacial location of an activated detector pixel forming a part of the portable detector in order to carry out a alignment method comprising the steps described herein.

An alignment method comprising the steps described herein.

The software encoded on the computer(s) employed in aspects of the invention that provide guidance on the orientation of the detector when out of alignment and distances to move the detector in order to bring it into alignment, will at least comprise executable code compiled from source code written in any conventional programming language, that employs one or more algorithms. In one aspect of the invention, the alignment software should be a data acquisition SDK, such as National Instruments LabView, Measurement Computing DASYLab or MathWorks MATLAB. The SDK's should offer the ability to generate stand-alone applications utilizing a vast selection of compatible input data. Data inputs will transfer by means of standard protocols such as RS 232 serial, USB 2.0, Ethernet, and or Wi-Fi.

All references cited in this specification are herein incorporated by reference as though each reference was specifically and individually indicated to be incorporated by reference. The citation of any reference is for its disclosure prior to the filing date and should not be construed as an admission that the present invention is not entitled to antedate such reference by virtue of prior invention.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

In various embodiments, functionality for implementing systems or methods of the present invention may be distributed among any number of client and/or server components. For example, various software modules may be implemented for performing various functions in connection with the present invention, and such modules may be variously implemented to run on server and/or client components.

The skilled person will be aware of a range of possible modifications of the various embodiments described above. Accordingly, the present invention is defined by the claims and their equivalents.

What is claimed is:

1. An alignment system, comprising:
A radiation source;
a portable detector comprising a plurality of detector pixels and operable to detect radiation from the radiation source;
an alignment computer comprising an alignment system and a communication unit wherein the communication unit is operable to communicate to the portable detector and the radiation source;
wherein the plurality of detector pixels are operable to be activated by a quantity or an intensity of alignment radiation beams;
wherein the alignment system designates at least a portion of the detector pixels as alignment pixels;
wherein the portable detector is operable to receive a plurality of the alignment radiation beams from the radiation source;
wherein upon, the alignment computer detects that the alignment pixels have been activated indicating that the portable detector is in an alignment condition with the radiation source, the alignment computer sends an activation signal to the radiation source to indicate that emission of radiation is permitted; and,
wherein the alignment computer prevents the emission of radiation from the radiation source until the portable detector is in the alignment condition.

2. The system of claim 1, wherein the emission of radiation from the radiation source is automatically performed upon and during achievement of the alignment condition.

3. The system of claim 2, further comprising:
a border detection module;
wherein the border detection module designates at least a portion of the plurality of detector pixels as border pixels.

4. The system of claim 3, wherein the border pixels are along a perimeter of the portable detector within a predefined range from an outer edge of the portable detector.

5. The system of claim 4, wherein upon activation of the border pixels by radiation from the radiation source, the alignment computer stops the radiation source from emission of radiation.

6. The system of claim 1, wherein the alignment computer is further configured to calculate a position of the radiation source relative to the position of the portable detector by analyzing the location of the activated detector pixels.

7. The system of claim 6, further comprising an indicator operable to communicate with the alignment computer, and adapted to notify an operator of if the portable detector is in an alignment condition or not.

8. The system of claim 7, wherein the radiation source or portable detector or both are adapted to move in all degrees of freedom.

9. The system of claim 8, wherein the radiation source or portable detector or both comprise a multi-axis motion sensor, the multi-axis motion sensor operable to calculate the movement of the radiation source or the portable detector or both.

10. The system of claim 9, wherein the alignment computer is further configured to send alignment data to the indicator based on the calculated position of the radiation source.

11. The system of claim 10, wherein the indicator is a visual indicator.

12. The system of claim 7, wherein the indicator is an audio indicator.

13. The system of claim 1, wherein the plurality of alignment radiation beams results from at least one or more configurable plates that are positioned between the radiation source and the portable detector to create a positioning aperture.

14. The system of claim 13, wherein the configurable plates comprise a collimator.

15. The system of claim 1, wherein the radiation source is capable of emitting radiation selected from the group consisting of single, pulse and continuance emissions.

* * * * *